(12) United States Patent
Masuda et al.

(10) Patent No.: US 12,690,834 B2
(45) Date of Patent: Jul. 28, 2026

(54) HEART VALVE ABNORMALITY DETECTION DEVICE, NON-TRANSITORY RECORDING MEDIUM, AND DETECTION METHOD

(71) Applicant: OSAKA UNIVERSITY, Suita (JP)

(72) Inventors: Hirotada Masuda, Suita (JP); Yoshiki Sawa, Suita (JP); Toru Kuratani, Suita (JP)

(73) Assignee: OSAKA UNIVERSITY, Suita (JP)

( * ) Notice: Subject to any disclaimer, the term of this patent is extended or adjusted under 35 U.S.C. 154(b) by 296 days.

(21) Appl. No.: 18/463,894

(22) Filed: Sep. 8, 2023

(65) Prior Publication Data

US 2023/0414192 A1     Dec. 28, 2023

Related U.S. Application Data

(63) Continuation of application No. PCT/JP2022/009637, filed on Mar. 7, 2022.

(30) Foreign Application Priority Data

Mar. 12, 2021     (JP) ................................. 2021-040718

(51) Int. Cl.
*A61B 7/04* (2006.01)
*A61B 5/00* (2006.01)
*A61B 5/02* (2006.01)

(52) U.S. Cl.
CPC ............ *A61B 7/04* (2013.01); *A61B 5/02007* (2013.01); *A61B 5/02028* (2013.01); *A61B 5/726* (2013.01); *A61B 5/7275* (2013.01)

(58) Field of Classification Search
CPC ....... A61B 7/04; A61B 5/02028; A61B 5/726; A61B 5/7275; A61B 5/02
See application file for complete search history.

(56) References Cited

U.S. PATENT DOCUMENTS

| | | |
|---|---|---|
| 2002/0001390 A1 | 1/2002 | Kawaguchi |
| 2004/0138572 A1* | 7/2004 | Thiagarajan ............. A61B 7/04 |
| | | 600/508 |

(Continued)

FOREIGN PATENT DOCUMENTS

| | | |
|---|---|---|
| JP | 2001-224563 A | 8/2001 |
| JP | 2004-529720 A | 9/2004 |

(Continued)

OTHER PUBLICATIONS

Written Opinion of the International Searching Authority of the corresponding International application No. PCT/JP2022/009637 mailed May 24, 2022 and English translation thereof.

(Continued)

*Primary Examiner* — Catherine M Voorhees

(74) *Attorney, Agent, or Firm* — Muncy, Geissler, Olds & Lowe, P.C.

(57) ABSTRACT

A heart valve abnormality detection device includes a heart sound data acquisition portion 21 configured to acquire heart sound data corresponding to heart sounds, a first processing portion configured to set, based on the heart sound data, a section between a first heart sound and a second heart sound of the heart sounds as a target range and acquire a peak frequency that is a peak value of a frequency in a frequency component of the heart sounds within the target range, and a second processing portion configured to output a detection signal indicating that there is a high probability of severe aortic stenosis in a case where the peak frequency is a peak reference value or greater.

21 Claims, 17 Drawing Sheets

(56)　　　　References Cited

U.S. PATENT DOCUMENTS

| | | | | |
|---|---|---|---|---|
| 2006/0142667 | A1* | 6/2006 | Munk | A61B 7/04 |
| | | | | 600/528 |
| 2017/0265838 | A1* | 9/2017 | Schulhauser | A61B 5/746 |
| 2018/0153415 | A1* | 6/2018 | Lee | A61B 5/6826 |
| 2020/0077892 | A1* | 3/2020 | Tran | G08B 21/02 |
| 2021/0251499 | A1* | 8/2021 | Ogawa | A61B 5/347 |
| 2022/0240796 | A1* | 8/2022 | Barnacka | A61B 7/00 |

FOREIGN PATENT DOCUMENTS

| | | | |
|---|---|---|---|
| JP | 2014-087543 A | 5/2014 | |
| JP | 2015-188512 A | 11/2015 | |
| JP | 2017-012366 A | 1/2017 | |
| JP | 2020-080894 A | 6/2020 | |
| WO | 02/096293 A1 | 12/2002 | |

OTHER PUBLICATIONS

International search report dated May 24, 2022 for corresponding PCT patent application No. PCT/JP2022/009637 and its English translation.

W. Reid Thompson, et al. Artificial Intelligence-Assisted Auscultation of Heart Murmurs: Validation by Virtual Clinical Trial. Pediatric Cardiology (2019) 40:623-629).

Isobe, Mitsuaki, Physical Examination for Valvular Heart Disease, Feb. 10, 2016,vol. 105,No. 2,pp. 184-191, [retrieved on May 10, 2022],Internet:<URL:https://doi.org/10.2169/naika.105.184>, Nihon Naika Gakkai Zasshi, Particularly,p. 187,left column.

Extended European search report dated Jul. 24, 2024 for corresponding European patent application No. 22767061.9.

El-Segaier M et al., Computer-Based Detection and Analysis of Heart Sound and Murmur, Jul. 1, 2005, vol. 33, No. 7, p. 937-942, Annals of biomedical engineering.

* cited by examiner

PEAK FREQUENCY DIAGNOSIS
OF SEVERE AS

HEALTHY

MODERATE

SEVERE

TIME:4,679
FREQUENCY:0.05063
AMPLITUDE:0.2271

HEALTHY

TIME[secs]

SEVERE

PEAK Hz OF THE 1st SOUND

HEART VALVE ABNORMALITY DETECTION DEVICE, NON-TRANSITORY RECORDING MEDIUM, AND DETECTION METHOD

TECHNICAL FIELD

The present invention relates to a heart valve abnormality detection device for detecting an abnormality in a heart valve such as aortic stenosis, a detection method, and a non-transitory computer readable storage medium.

BACKGROUND ART

With the aging of the population in recent years, the number of patients with valvular heart disease, in particular, severe aortic stenosis (AS), is increasing. Aortic stenosis is a heart disease in which an aortic valve is calcified with aging, causing the valve to stiffen and become difficult to open to thereby significantly reduce the amount of blood pumped into the aorta. Since aortic stenosis is a serious disease that can lead to sudden death or heart failure, overlooking aortic stenosis is a major medical problem. It is said that 3.4% of elderly people aged 75 years and over are affected with severe AS, and the number thereof is said to be as high as 560,000 in Japan.

Auscultation widely used in clinical practices is useful for screening for valvular disease; however, it is said that non-cardiologists with limited experience in auscultation have low diagnostic accuracy of valvular disease and the diagnostic accuracy is about 40 to 50%. One of the reasons for the low diagnostic accuracy of auscultation is that the timing, location, and range of heart murmurs vary depending on the type and condition of valvular disease, and it is difficult to comprehensively judge based on such pieces of information.

Conventionally, a technology has been proposed for detecting an abnormality in a heart valve by analyzing heart sound information acquired from a stethoscope and the like. Patent Literature 1 discloses extracting the first heart sound signal and the second heart sound signal from heart sound data based on heart sounds of a living body, and making diagnosis of a heart disease based on a comparison, as for the first heart sound signal and the second heart sound signal, of amplitude and power of a specific frequency band with the reference values.

Patent Literature 2 discloses detecting heart murmurs from collected heart sounds, generating an analytic signal using an interval between the heart murmurs, and classifying cases of the heart murmurs based on a comparison between a first frequency component that is a predetermined frequency component of the analytic signal and a second frequency component that is a frequency component constituting a part of the first frequency component. Patent Literature 2 describes, in paragraph 0026, determining mitral valve insufficiency or aortic stenosis based on a frequency band power ratio.

Patent Literature 3 discloses diagnosing the presence or absence of a heart disease based on the shape of a power spectrum in some frequency bands of data on systolic heart sounds.

Further, in order to detect heart murmurs, an approach has been proposed of using a technique such as deep learning to analyze sound sources acquired with a digital stethoscope and detecting various heart diseases (Non-Patent Literature 1).

CITATION LIST

Patent Literature

Patent Literature 1: Japanese Patent Application Laid-Open No. 2017-012366

Patent Literature 2: Japanese Patent Application Laid-Open No. 2014-087543

Patent Literature 3: Japanese Patent Application Laid-Open No. 2015-188512

Non-Patent Literature

Non-Patent Literature 1: W. Reid Thompson, et al. Artificial Intelligence-Assisted Auscultation of Heart Murmurs: Validation by Virtual Clinical Trial. Pediatric Cardiology (2019) 40:623-629)

SUMMARY OF INVENTION

Technical Problem

However, in the conventional technologies, it is impossible to diagnose an abnormality in a heart valve, in particular, severe aortic stenosis (AS), using simple processing with high accuracy.

For example, in the case of Patent Literature 1, a heart disease is diagnosed by comparing the amplitude and power of a specific frequency band of each of the first heart sound signal and the second heart sound signal with the reference values. Therefore, the number of detection parameters used for the comparison increases, so that the load on arithmetic processing is increased and errors can easily accumulate. The same applies to the case of Patent Literature 2, and further, the technology can merely classify cases. Further, in the case of Patent Literature 3, diagnosis is made based on the comparison in shape of the power spectrum. It is therefore difficult to achieve a high degree of accuracy because ambiguity remains in the determination, and at most, the presence or absence of a heart disease can be determined using the technology.

Early detection through accurate diagnosis is important because even valvular disease is sometimes advanced without obvious subjective symptoms, and if it is severe AS, the only treatment method is surgery. In specialized facilities such as large hospitals, echocardiography is used to accurately assess the severity of valvular disease. In contrast, such an approach is not easily made in small clinics in terms of cost-effectiveness because the approach involves equipment and specialists.

In the current situation where a screening to determine whether echocardiography is necessary is not sufficiently performed through auscultation, a simple detection device that is accurate, reliable, and provides clear results is desired.

The present invention has been achieved in light of such a problem, and therefore, an object of the present invention is to detect, as a clear result, an abnormality in a heart valve, in particular, severe aortic stenosis, simply and with high accuracy.

Solution to Problem

According to a first aspect of the present invention, a heart valve abnormality detection device includes a heart sound data acquisition portion configured to acquire heart sound data corresponding to heart sounds, a first processing portion configured to set, based on the heart sound data, a section between a first heart sound and a second heart sound of the heart sounds as a target range and acquire a peak frequency that is a peak value of a frequency in a frequency component of the heart sounds within the target range, and a second processing portion configured to output a detection signal indicating that there is a high probability of severe aortic stenosis in a case where the peak frequency is a peak reference value or greater.

Preferably, the heart valve abnormality detection device includes an ejection time acquisition portion configured to acquire an ejection time based on the heart sound data, in which the second processing portion outputs the detection signal in a case where, in addition to a condition that the peak frequency is the peak reference value or greater, a condition that the ejection time is an ejection reference value or greater is satisfied.

More preferably, the heart valve abnormality detection device includes a detection portion configured to detect, based on the heart sound data, ejection click occurring in a vicinity of the first heart sound, in which the second processing portion outputs the detection signal in a case where, in addition to a condition that the peak frequency is the peak reference value or greater, a condition that the ejection click is detected is satisfied.

More preferably, the first processing portion acquires the peak frequency by performing wavelet analysis on the heart sound data.

According to a second aspect of the present invention, a heart valve abnormality detection device includes a first processing portion configured to set, based on the heart sound data, a section between a first heart sound and a second heart sound of the heart sounds as a target range and acquire a peak frequency that is a peak value of a frequency in a frequency component of the heart sounds having an intensity equal to or greater than a reference intensity within the target range, and a second processing portion configured to output a detection signal indicating that a heart valve has a severe abnormality in a case where the peak frequency is a peak reference value or greater.

According to a third aspect of the present invention, a heart valve abnormality detection device includes a first processing portion configured to set, based on the heart sound data, a section between a first heart sound and a second heart sound of the heart sounds as a target range and acquire a peak frequency that is a peak value of a frequency in a frequency component of the heart sounds having an intensity equal to or greater than a reference intensity within the target range, an ejection time acquisition portion configured to acquire an ejection time based on the heart sound data, and a second processing portion configured to output a detection signal indicating a degree of the abnormality in the heart valve based on a result of comparison between the peak frequency and a set frequency range and a result of comparison between the ejection time and an ejection reference value.

Advantageous Effects of Invention

According to the present invention, it is possible to detect, as a clear result, an abnormality in a heart valve, in particular, severe aortic stenosis, simply and with high accuracy.

According to the third aspect of the present invention, it is possible to detect, as a clear result, a degree of an abnormality in a heart valve simply and with high accuracy.

BRIEF DESCRIPTION OF DRAWINGS

FIG. 6 is a conceptual diagram of an example of peak frequency diagnosis of severe AS.

DESCRIPTION OF EMBODIMENTS

Principle of the Present Invention

First, the principle of the present invention is described.

Figure 3:
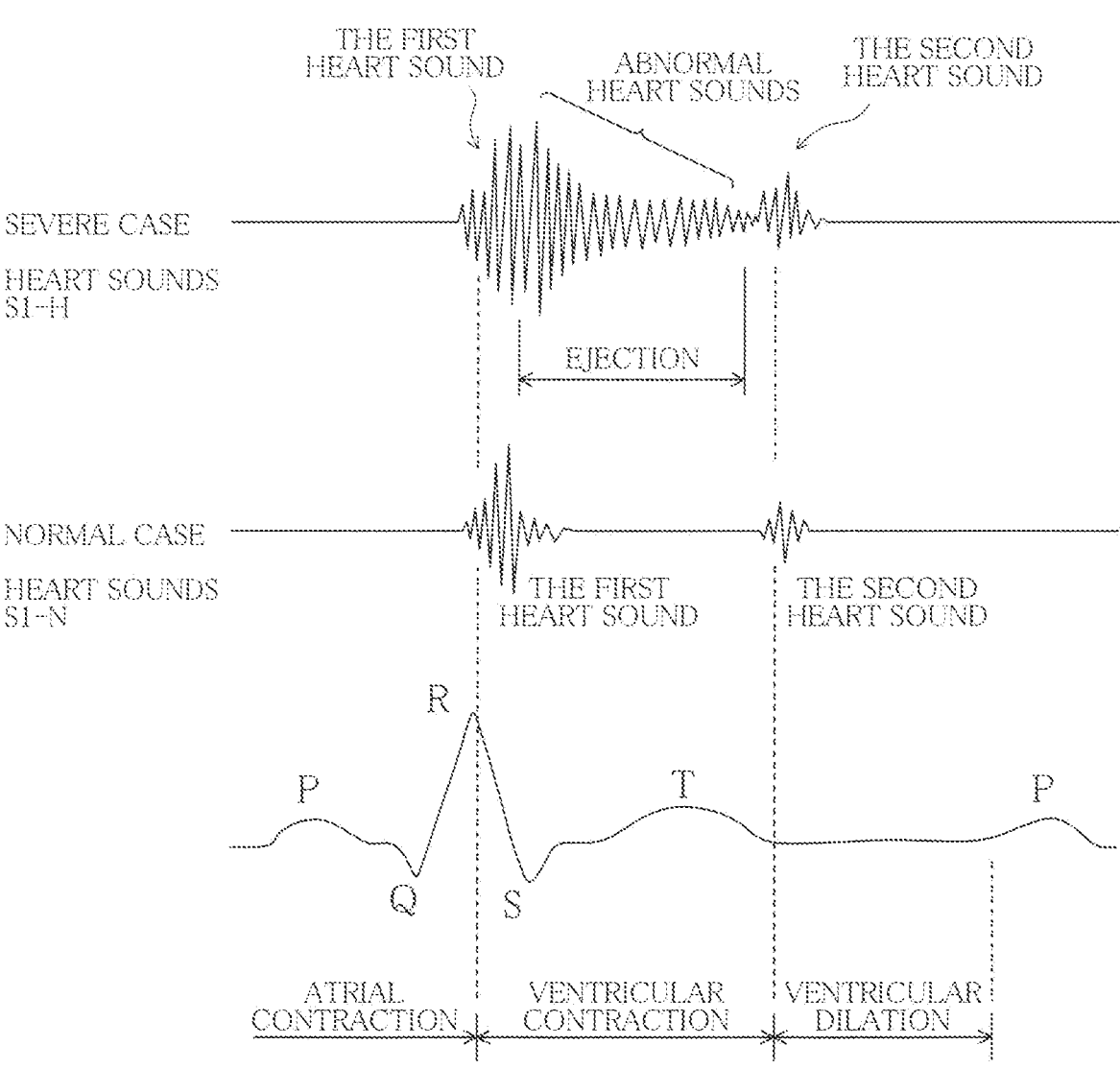
FIG. 3 is a diagram illustrating an example of heart sounds acquired from a heart sound sensor.
Figure 4:
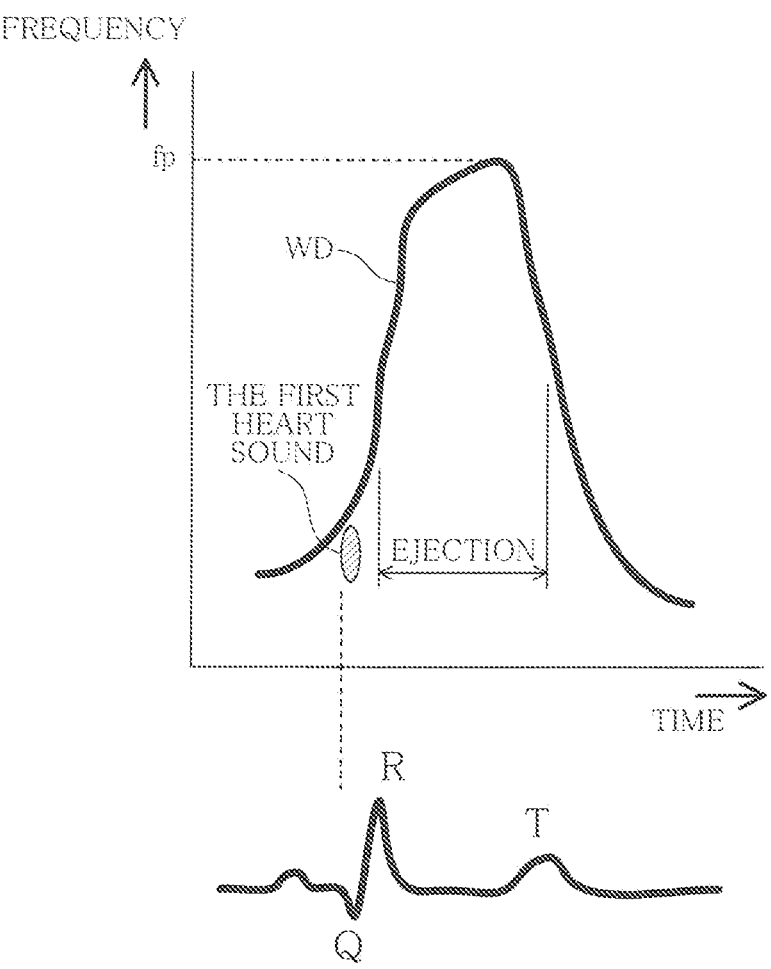
FIG. 4 is a diagram schematically illustrating an example of a frequency component of heart sounds by wavelet analysis.

FIG. 3 is a diagram illustrating an example of heart sounds acquired from a heart sound sensor, and FIG. 3 illustrates heart sounds S1-H of a patient with severe aortic stenosis (AS) and heart sounds S1-N of a healthy individual along with an electrocardiogram. FIG. 4 is a diagram schematically illustrating an example of a frequency component of heart sounds by wavelet analysis, and FIG. 4 schematically illustrates a result of the wavelet analysis by a contour line WD in the scalogram.

Aortic stenosis (AS) is a disease in which calcification of the aortic valve causes the aortic valve to stiffen and become difficult to open. As a result, it takes longer than usual for blood to pass through the narrow valve opening. A turbulent flow generated at this time generates a high-pitched noise. Then, as the blood passes through the narrowed lumen, the blood flow rate increases, which generates a high-pitched white noise. In other words, as the disease becomes more severe, the high-pitched noise has higher frequency components. In echocardiography, an increase in blood flow rate at the site of stenosis is used as an indicator of the severity.

In the present invention, instead of the echocardiography, heart sounds acquired through auscultation are used as a sound source, wavelet analysis is performed on heart sound data acquired from the heart sounds to detect an increase in frequency (high-pitched sound) in a specific section to thereby detect severe aortic stenosis (severe AS). For determination as to whether a patient has severe AS, a peak frequency in the specific section is detected for assessment.

As illustrated in FIG. 3, the focus is on the fact that abnormal heart sounds occur between the first heart sound and the second heart sound in severe AS, and wavelet analysis is performed on the abnormal heart sounds. The wavelet analysis is performed, so that a peak frequency fp appears somewhere in an ejection phase as illustrated in FIG. 4, for example. The peak frequency fp is detected and the detected peak frequency fp is assessed.

Further, the focus is on the fact that a blood ejection time is extended as AS becomes more serious, and wavelet analysis is performed to obtain a heart ejection time. The obtained ejection time is assessed and utilized for detection of severe AS. Further, a frequency of the main component of the first heart sound acquired from the heart sounds is assessed to detect the presence or absence of the occurrence of ejection click. The presence or absence of ejection click is utilized for detection of severe AS.

As described above, according to the present invention, a specific acoustic pattern in heart sounds is used to detect severe AS accurately.

In order to verify the accuracy of the detection according to the present invention, an assessment was made based on the peak frequency and the ejection time by using 85 cases of severe AS and 100 cases of non-AS as the target group. As a result, the detection rate of severe AS was increased to as much as 90%.

It was found out that the peak frequency and the ejection time are positively correlated with the severity of AS; therefore, moderate AS can also be detected by performing wavelet analysis on heart sounds. In other words, according to the present invention, the severity of AS can be diagnosed.

No technique has ever been able to achieve classification of the severity of AS only through auscultation. The use of the technique of the present invention makes it possible, even for a physician who has little experience in listening to heart murmurs, to easily diagnose the severity of AS. Further, the technique of the present invention enables a patient to detect AS by himself/herself by using a digital stethoscope at home. This allows for a referral to a specialized facility and treatment thereat, and it is expected to reduce the number of patients who suddenly die from AS.

In a specialized facility, a patient with moderate AS may be requested to come to the facility for echocardiography for follow-ups about once every six months. In contrast, the technique of the present invention enables detection of the progression of AS through auscultation only. The technique is therefore expected to replace echocardiography. This can keep the inspection cost under control, leading to the reduction in medical expenses.

The present invention is applicable also to detection of other valvular diseases such as mitral valve insufficiency and aortic valve insufficiency.

Hereinafter, embodiments of the present invention will be described.

(Flow of Diagnosis Supported by Heart Valve Abnormality Diagnosis System)

Figure 1:
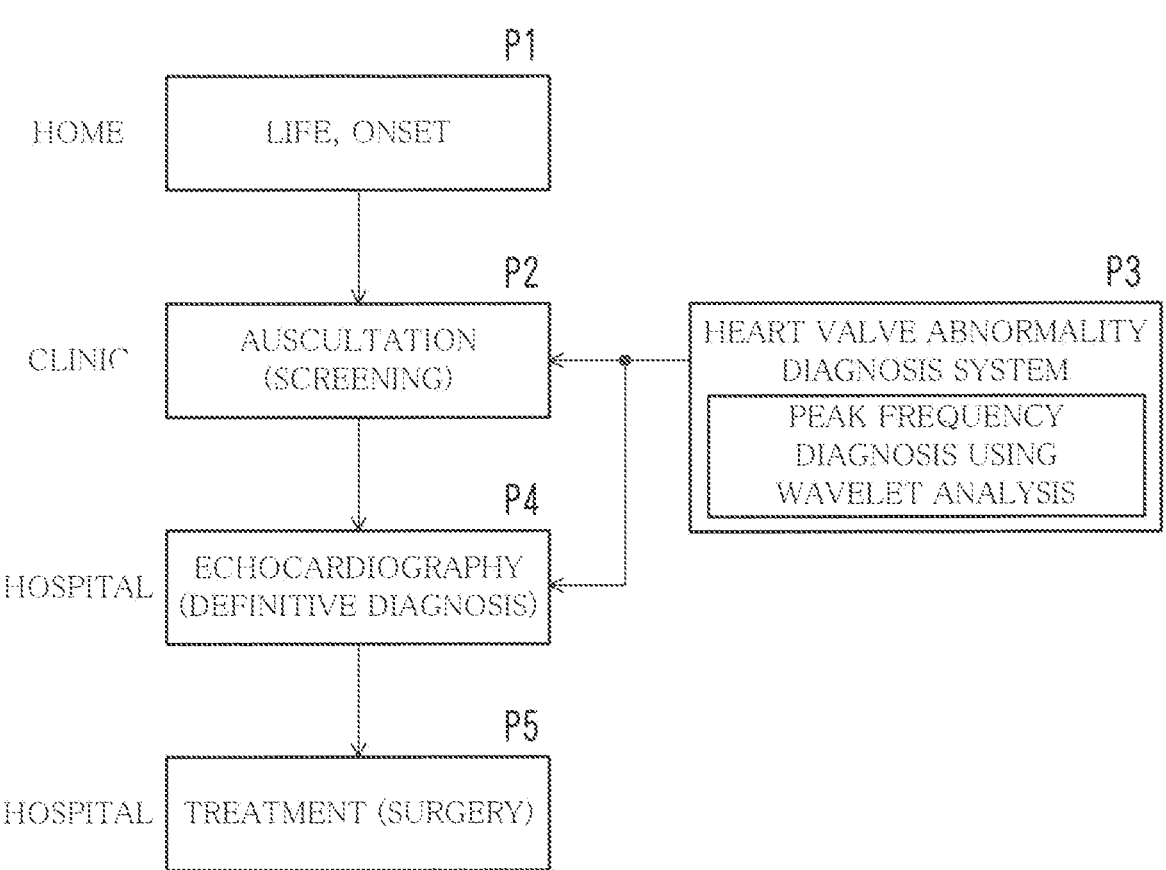
FIG. 1 is a diagram illustrating a process from diagnosis of aortic stenosis to treatment thereof.

FIG. 1 is a diagram illustrating the flow from diagnosis of aortic stenosis to treatment thereof.

Referring to FIG. 1, for example, a patient with a chronic heart disease who is discharged from a hospital to take care of his/her health lives around his/her house or in the community (P1). If any symptoms appear in the patient, he/she visits his/her family clinic for a checkup (P2). The clinic is equipped with a heart valve abnormality detection device, and a heart valve abnormality diagnosis system 1 is configured together with the peripheral devices, for example. The heart valve abnormality diagnosis system 1 makes peak frequency diagnosis by wavelet analysis, detects an abnormality in a heart valve, in particular, severe aortic stenosis, with high accuracy, and outputs the detection result for display. A physician performs a medical examination including auscultation with a stethoscope, and makes final diagnosis of the heart disease with the assistance of the heart valve abnormality diagnosis system 1 (P3).

In a case where the physician diagnoses the patient, for example, as having a high suspicion of severe AS, the patient goes to a hospital for echocardiography for example, and definitive diagnosis is made in the hospital (P4). Once the diagnosis of severe AS is confirmed, the patient undergoes surgery such as artificial valve replacement, valvuloplasty, or catheterization and receives treatment (P5).

In the heart valve abnormality diagnosis system 1, a heart valve abnormality detection device 5 is connected to a hospital, a specialized facility, and the like via a network to exchange various pieces of information. For example, the detection result by the heart valve abnormality detection device 5 is transmitted to an echocardiography laboratory and an operating room in the hospital and is displayed therein, and the result of echocardiography or surgery is received and used for learning in the heart valve abnormality detection device 5 and for setting parameters therein.

As described above, the heart valve abnormality diagnosis system 1 is configured centering on a heart valve abnormality detection device equipped in a clinic or the like. This enables severe AS to be easily found out by auscultation, leading to a life-saving flow such as the subsequent definitive diagnosis and treatment. Thus, the life-saving rate of patients with AS can be greatly improved.

(Configuration of Heart Valve Abnormality Diagnosis System)

Figure 2:
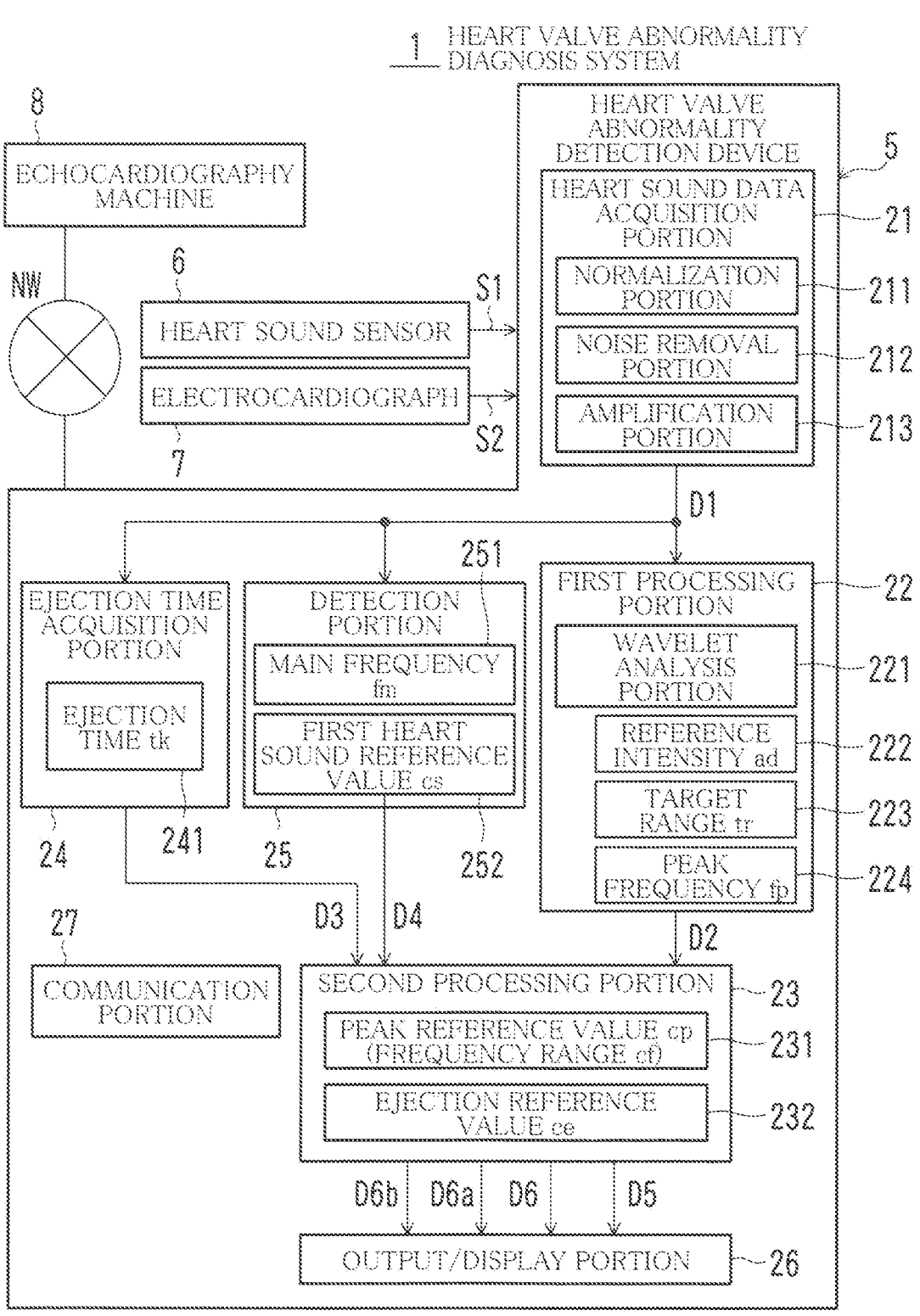
FIG. 2 is a block diagram illustrating an example of the configuration of a heart valve abnormality diagnosis system according to an embodiment of the present invention.

FIG. 2 illustrates an example of the configuration of the heart valve abnormality diagnosis system 1 according to an embodiment of the present invention.

Referring to FIG. 2, the heart valve abnormality diagnosis system 1 includes the heart valve abnormality detection device 5, a heart sound sensor 6, and an electrocardiograph 7, and the heart valve abnormality diagnosis system 1 is connected to an echocardiography machine 8 and so on via a network NW.

The heart sound sensor 6 is an acoustoelectric transducer such as a microphone, a piezoelectric sensor, or an acceleration sensor, and outputs a heart sound signal S1 corresponding to heart sounds of a patient. The heart sound signal S1 includes signals corresponding to the first heart sound, the second heart sound, and a heart murmur. The heart sound sensor 6 may be a heart sound sensor integrated into a stethoscope. The heart sound sensor 6 is placed on, for example, the second intercostal space right sternal border, Erb's area, under the papilla, or the like of the patient to acquire the heart sounds.

The electrocardiograph 7 is used to acquire an electrocardiogram of the patient, and outputs an electric signal (electrocardiogram signal) S2 including signals of P, Q, R, S, T, U, and P waves.

The echocardiography machine 8 is used to acquire images and cross-sectional images of the heart and blood vessels by using ultrasonic waves and to examine abnormalities in structures and functions of the individual parts. The echocardiography machine 8 is installed in a hospital or a specialized facility.

In the meantime, the heart valve abnormality detection device 5 includes a heart sound data acquisition portion 21, a first processing portion 22, a second processing portion 23, an ejection time acquisition portion 24, a detection portion 25, an output/display portion 26, and a communication portion 27.

All or some of the portions of the heart valve abnormality detection device 5 can be implemented by an information processing apparatus such as a server or a personal computer. The individual functions of the heart valve abnormality detection device 5 described below can be achieved by a CPU executing a computer program, or, by cooperation between the CPU and a hardware element or a device. The computer program can be executed after being read out of a recording medium or after being downloaded from a server. The output/display portion 26 and the communication portion 27 can be implemented by a display device and a communication function provided in the information processing apparatus, respectively.

[Heart Sound Data Acquisition Portion]

Figure 5:
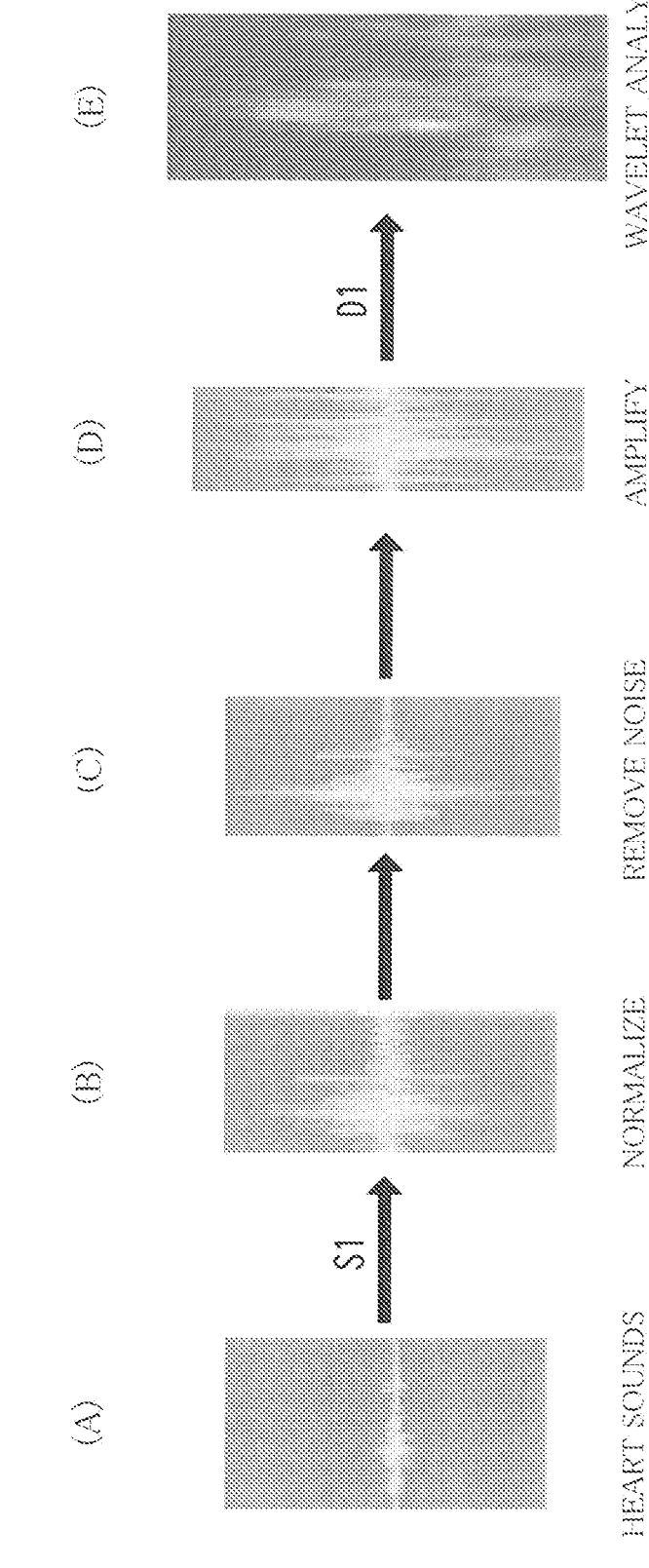
FIG. 5 is a diagram illustrating an example of the flow of processing on a heart sound signal up to wavelet analysis.

FIG. 5 is a diagram illustrating an example of the flow of processing on a heart sound signal up to wavelet analysis.

The heart sound data acquisition portion 21 serves to acquire heart sound data D1 corresponding to the heart sounds to output the heart sound data D1, and includes a normalization portion 211, a noise removal portion 212, and an amplification portion 213. The heart sound signal S1 inputted is an analog signal or a digital signal. In a case where the heart sound signal S1 is an analog signal, an appropriate AD converter is used to convert the analog signal to a digital signal, and then the subsequent processing is performed.

The normalization portion 211 normalizes the heart sounds in order to deal with the difference in loudness of the heart sounds.

The noise removal portion 212 removes environmental noises including an ambient sound and an electrical noise irrelevant to the heart sounds. Further, the heart sounds sometimes contain, as noises, breath sounds, and it is further preferable to remove such breath sounds from the heart sounds.

The amplification portion 213 amplifies the heart sound signal S1 by 16 times for example, so that the heart sound signal S1 reaches a predetermined intensity level (amplitude level). The amount of amplification is adjustable. Thereby, the heart sound data D1 outputted by the heart sound data acquisition portion 21 indicates a waveform corresponding to the heart sounds, and the amplitude of various frequency components included in the waveform is normalized.

[First Processing Portion]

The first processing portion 22 sets, based on the heart sound data D1, a section between the first heart sound and the second heart sound of the heart sounds as a target range, and acquires a peak frequency fp that is a peak value of the frequency of the heart sounds having an intensity (amplitude) equal to or greater than a reference intensity within the target range.

The first processing portion 22 includes a wavelet analysis portion 221, a reference intensity storage portion 222, a target range storage portion 223, and a peak frequency storage portion 224.

The wavelet analysis portion 221 performs continuous wavelet transform on the heart sound data D1 inputted, and localizes both components of a time and a frequency of the heart sound data D1. The continuous wavelet transform is performed to acquire a feature amount of the time-frequency of the heart sound data D1, i.e., the frequency with respect to a temporal axis and the intensity (amplitude) of each of the frequency components. For example, analytical data is acquired in which a time t, a frequency f, and an intensity (amplitude) dB of each frequency component in the heart sound data D1 are represented as an x-axis, a y-axis, and a z-axis, respectively. The analytical data can be represented on a two-dimensional plane using a scalogram as in FIGS. 8 to 12 described later. In the scalogram, the horizontal axis represents a time and the vertical axis represents a frequency. The brightness or color of each point represents an intensity (amplitude) of a certain frequency at a certain time point.

In the meantime, various parameters and coefficients acquired by the wavelet analysis portion 221 can be used as a feature value of machine learning using artificial intelligence (AI).

The reference intensity storage portion 222 stores, therein, a reference intensity ad with which to determine the peak frequency fp. The condition for the reference intensity ad is that, in the case of acquiring the peak frequency fp, the intensity of the frequency component is the reference intensity ad or greater. The reference intensity ad is used in order to acquire a correct frequency component by removing the influence of noise components or harmonic components remaining in the heart sound data D1. The reference intensity ad can be determined by conducting an experiment so that the correct frequency component is empirically acquired. As long as there are no noise components or harmonic components at all or the noise components or harmonic components are negligible, a value close to 0 (zero) can be used as the reference intensity ad for example, or, alternatively, the reference intensity ad can be excluded from the condition.

In a case where there is a signal having an intensity higher than that of the peak frequency near the frequency that is half of the peak frequency acquired by the wavelet analysis, the higher signal corresponds to a fundamental wave, and that frequency is used as the peak frequency fp and the harmonic is excluded. In addition, it is possible to empirically exclude one that is doubtful as the peak frequency fp.

In short, it is important to acquire, as the peak frequency fp, a significant value for a frequency component whose intensity is not 0 (zero).

The target range storage portion 223 stores, therein, a temporal target range tr with which the peak frequency fp is determined. As the target range tr, a temporal range within which the aortic valve is open and the blood flows therethrough is preferably set. However, since the target range tr is used for determining the peak frequency fp in the temporal range, the target range tr does not necessarily have to match the temporal range of actual blood flow as long as a significant peak frequency fp is extracted.

A method for setting the target range tr is exemplified. For example, the range between the start of the first heart sound and the end of the second heart sound, which is a range corresponding to ventricular systole, is set as the target range tr. Further, considering that the first heart sound is loud at the timing when the mitral valve opens and that it takes time for blood to start flowing actually, a range after the time t1 has elapsed since the start of the first heart sound is set as the target range tr. Further, considering the extension of the ejection time and a time period during which the peak frequency fp may actually be detected, a range after the time t1 has elapsed since the start of the first heart sound to the time t2 or shorter is set as the target range tr. Further, in a case where the second heart sound is not clearly identified, a range after the time t1 has elapsed since the start of the first heart sound but not exceeding the time t2 is set as the target range tr. In short, the target range tr is limited temporally.

Further, the electrocardiogram signal S2 is used and a range from the position of the S wave to the start or end of the second heart sound is set as the target range tr.

To be specific, for example, it is possible that the time t1 is set at 100 ms, the time t2 is set at 500 ms, and the target range tr is set to a range after 100 ms from the start of the first heart sound but not exceeding 500 ms. The times other than those may be used. According to the method for setting, the target range tr can be set only based on the heart sound data D1 without using the electrocardiogram signal S2. Further, even if the second heart sound is unclear, the target range tr can be identified.

The peak frequency storage portion 224 stores, therein, the peak frequency fp acquired. In acquiring the peak frequency fp, it is possible to acquire only one peak frequency fp; however, an inappropriate peak frequency having a large error, for example, might be extracted. In other words, the heart sounds vary for each pulse wave (aortic wave) and the peak frequency fp may also vary. Further, in a case where arrhythmia occurs, or where the pulse slows down, the peak positions do not match. To address this, it is preferable to acquire a plurality of peak frequencies to use the mean value or the like in order to increase the reliability of the peak frequency fp.

Thus, in order to determine a representative value used as the peak frequency fp, for example, the mean value of a plurality of peak frequencies acquired from the target range tr for each of the plurality of pulse waves is determined to be the representative value of the peak frequency fp. Alternatively, for example, five peak frequencies are acquired from the target range tr for each of five consecutive pulse waves and the mean value of the five peak frequencies is determined to be the representative value of the peak frequency fp. Alternatively, the top n, for example, the top five, of a plurality of peak frequencies acquired from the target range tr are selected and the mean value of the five peak frequencies is determined to be the representative value of the peak frequency fp. Alternatively, from the maximum ten peak frequencies acquired from the target range tr for each of 10 consecutive pulse waves, the maximum value, the minimum value, and the other singular values are excluded, and the mean value of the remaining, for example, five peak frequencies is determined to be the representative value of the peak frequency fp. Alternatively, instead of the mean value, the mean-square or the median value may be used, or the representative value may be determined by using an appropriate selection algorithm. Alternatively, in a case where the breath sounds are mixed in the heart sound data D1, it is preferable to determine the representative value by using a peak frequency acquired only from the target range tr that does not overlap with the time for the breath sounds.

The first processing portion 22 outputs peak data D2 including the peak frequency fp acquired as described above to the second processing portion 23.

The ejection time acquisition portion 24 acquires an ejection time tk based on the heart sound data D1. The ejection time tk thus acquired is stored into an ejection time storage portion 241 and is outputted as ejection data D3.

The ejection time tk is the time during which blood flows out of the aortic valve and corresponds to an ejection phase due to ventricular contraction. Since the ejection phase is usually, of the ventricular systole from the first heart sound to the second heart sound, a period after the ventricular pressure is higher than the intra-aortic pressure and the aortic valve opens, the ejection time tk can be acquired by detecting the timing at which the aortic valve opens and the timing of the second heart sound based on the heart sound data D1.

The ejection time tk is approximately 200 ms in a healthy individual; however, the ejection time tk increases as the disease becomes more severe. For example, in the case of severe AS, the ejection time tk increases to approximately 300 ms to 500 ms. There is not much difference between individuals.

In the meantime, since the ejection time tk is used for comparison with an ejection reference value ce, the ejection time tk does not necessarily match the actual ejection time for a patient. In short, it is only required that the ejection time tk has a value corresponding to the ejection time for the patient. It is thus possible that, for example, a time between the first heart sound and the second heart sound is acquired as the ejection time tk and an appropriate value of the ejection reference value ce is set accordingly for comparison.

The detection portion 25 detects, based on the heart sound data D1, the main component of the first heart sound, namely, the frequency of a sound having a high intensity in the vicinity of the first heart sound. A main frequency fm that is the detected frequency is stored into a main frequency storage portion 251.

Further, a first heart sound reference value cs is stored in a first heart sound reference value storage portion 252. In a case where the main frequency fm is the first heart sound reference value cs or greater, click data D4 indicating that ejection click has occurred is output to the second processing portion 23.

The first heart sound in the heart sounds is usually a sound made when the mitral valve gets closed, and immediately after the closure of the mitral valve, the aortic valve opens. However, when the aortic valve stiffens and does not work properly, the aortic valve does not open easily. Therefore, the aortic valve opens upon impact when blood pushed out due to the ventricular contraction hits the aortic valve. At this time, ejection click which has a sound higher than a normal first heart sound occurs. In other words, the ejection click indicates that stiffening of the aortic valve is progressing and the function of the aortic valve is deteriorating.

The main frequency component of the ejection click was examined and found to be in the range of 50 to 60 Hz. Since the ejection click occurs immediately after the first heart sound, the first heart sound sounds higher on the stethoscope and the ejection click is detected as being integrated with the first heart sound in the heart sound data D1. In normal heart sounds of a healthy individual, the first heart sound includes frequency components of 30 to 40 Hz. In the case of severe AS, the early stage of the first heart sound includes frequency components of 40 Hz or greater.

In light of the above, in order to detect ejection click, the first heart sound reference value cs is set at, for example, 50 Hz, 55 Hz, 60 Hz, or the like. In a case where the first heart sound reference value cs is set at 50 Hz, which is the low one, the detection sensitivity is increased and the possibility of erroneously detecting a sound that is not ejection click is increased, but the possibility of failing to detect ejection click is reduced. Therefore, the accuracy of detection of severe AS is improved by performing an ANDing operation with other conditions. In a case where the first heart sound reference value cs is set at 60 Hz, which is the high one, the detection sensitivity is reduced. However, if the click data D4 is detected, there is a high probability that stiffening of the aortic valve is progressing and the patient has severe AS. Therefore, the first heart sound reference value cs should be determined in the light of the above. Further, it is also possible to change a weight of the click data D4 for the detection of severe AS depending on the value of the first heart sound reference value cs.

As described above, the ejection click is detected by focusing on the fact that the frequency of the main component of the sound is high. This enables detecting an abnormality in a heart valve including severe AS with high accuracy.

[Second Processing Portion and Peak Frequency Diagnosis]

The second processing portion 23 detects, based on the peak data D2, the ejection data D3, and the click data D4, an abnormality in the heart valve, in particular, severe AS, by selecting a determination mode to combine the following Conditions 1 to 3.

(Condition 1) A case where the peak frequency fp is a peak reference value cp or greater.

(Condition 2) A case where the ejection time tk is the ejection reference value ce or greater.

(Condition 3) A case where the main frequency fm is the first heart sound reference value cs or greater, that is, a case where ejection click is detected.

According to the present embodiment, in a determination mode 1, if Condition 1 is satisfied, then it is determined that there is a high probability of severe AS and a detection signal D5 indicating the fact is output. In a determination mode 2, if Condition 1 and Condition 2 are satisfied at the same time, then it is determined that there is a high probability of severe AS and the detection signal D5 indicating the fact is output. In a determination mode 3, if Conditions 1, 2, and 3 are satisfied at the same time, then it is determined that there is a high probability of severe AS and the detection signal D5 indicating the fact is output.

In response to the output of the detection signal D5, the output/display portion 26 displays, on a screen, a message indicating that there is a high probability of severe AS, and if necessary, makes a sound such as an alarm, and sends a message to another device via the communication portion 27 and the network NW. For example, the message "severe AS is suspected" is displayed on the screen.

Further detailed descriptions are provided below.

In the second processing portion 23, the peak reference value cp and the ejection reference value ce are stored in the respective storage portions 231 and 232. Further, the second processing portion 23 includes an operation portion and a setting portion (both not shown) for switching between the determination modes for setting.

In the determination mode 1, in a case where the peak frequency fp is the peak reference value cp or greater, it is determined that there is a high probability of severe AS, and the detection signal D5 indicating the fact is output. The peak reference value cp is assumed to be 300 Hz, for example. Stated differently, in a case where the peak frequency fp is 300 Hz or greater, the detection signal D5 is output.

Based on the empirical study of previous cases, the peak frequency fp in cases of severe AS was 250 Hz or greater and a mean value thereof was 320 Hz or so, with a variation of plus or minus 50 Hz or so. Accordingly, the peak reference value cp is set at 300 Hz, and severe AS is detected in a case where the peak frequency fp is 300 Hz or greater, leading to detection of most cases of severe AS. However, even if the peak frequency fp is 300 Hz or greater, it does not necessarily mean that the patient has severe AS. In this respect, it is necessary to wait for a combination with other conditions or wait for a medical operation such as an echocardiographic examination.

As described above, according to the determination mode 1, the detected peak frequency fp is compared with the peak reference value cp, focusing on the fact that the peak frequency fp is high in the case of severe AS. In a case where the peak frequency fp is, for example, 300 Hz or greater, the detection signal D5 is output. This enables detecting a patient who is highly likely to have severe AS with considerable accuracy.

In a case where the peak reference value cp is set at a value higher than 300 Hz, for example, 320 Hz or 340 Hz, a possibility that a patient having severe AS is not detected increases; however, a possibility that a patient is detected to have severe AS despite the fact that he/she does not have severe AS is reduced. It is thus preferable to set the peak reference value cp in consideration of this point and a combination with other conditions that make up for this point.

In the determination mode 2, in addition to the condition for the peak frequency fp, in a case where the ejection time tk is the ejection reference value ce or greater, it is determined that there is a high probability of severe AS, and the detection signal D5 indicating the fact is output. The ejection reference value ce is set at 300 ms, for example.

As described above, a patient with severe AS has an extended ejection time, and it is a value ranging from 300 to 460 ms or so based on the empirical values. Therefore, the ejection reference value ce is set at 300 ms, which is the low value, and an ejection time tk of 300 ms or greater is added to the condition for detection of severe AS. Thereby, the accuracy that the detection signal D5 is output in a case where a patient actually has severe AS is increased, and the reliability of detection is improved.

As described above, according to the determination mode 2, in a case where Condition 1 and Condition 2 are satisfied, specifically, in a case where the peak frequency fp is 300 Hz or greater for example, and further, in a case where the ejection time tk is 300 ms for example, the detection signal D5 is output. This enables detecting a patient who is highly likely to have severe AS more accurately.

As mentioned above, since there are errors and variations also in acquiring the actual ejection time tk, it is preferable to set an appropriate ejection reference value ce according to the errors and variations in acquiring the ejection time tk, or according to the method for acquiring the ejection time tk.

In the determination mode 3, in addition to the condition for the peak frequency fp and the condition for the ejection time tk, in a case where the main frequency fm is the first heart sound reference value cs or greater, namely, the occurrence of ejection click is used as a condition, it is determined that there is a high probability of severe AS, and the detection signal D5 indicating the fact is output.

As described above, the ejection click indicates that stiffening of the aortic valve is progressing and the function of the aortic valve is deteriorating, and the occurrence of ejection click means that the patient may have severe AS. Accordingly, the occurrence of ejection click is added, as Condition 3, to Condition 1 and Condition 2. This enables acquiring a detection signal D5 having a higher reliability, leading to the detection of a patient who is highly likely to have severe AS with higher accuracy.

Since the detection accuracy and detection sensitivity of the ejection click vary depending on the value of the first heart sound reference value cs, the first heart sound reference value cs is set also in consideration of the relevance to and compatibility with other conditions. This enables detection of severe AS with extremely high accuracy.

In addition to the determination modes 1 to 3 described above, determination modes in which Conditions 1 to 3 are combined in various ways can be set. For example, it is possible to combine Condition 1 with Condition 3, or, to combine Condition 2 with Condition 3. Alternatively, conditions other than Conditions 1 to 3 may also be combined.

Further, it is possible to change, depending on the values of the peak frequency fp, the ejection time tk, and the main frequency fm acquired in other conditions and the determination results, the settings of the ejection reference value ce, the first heart sound reference value cs, the peak reference value cp, and so on in those other conditions. In such a case, the order of application of Conditions 1 to 3 may be set in various ways, and one condition may be applied a plurality of times.

Further, the second processing portion 23 also has a determination mode 4 for detecting the severity of AS. To be specific, in the determination mode 4, the severity of AS is determined by comparing the detected peak frequency fp with a set frequency range cf. Here, an example will be described in which the detection signal D5 is output in the case of severe AS and a detection auxiliary signal D6 is output in the case of moderate AS.

As the frequency range cf, a first frequency for determining severe AS and a second frequency for determining moderate AS are set. As the first frequency, the peak reference value cp may be used. If the peak frequency fp is the first frequency or greater, then it is determined that the patient has severe AS. If the peak frequency fp is smaller than the first frequency and is equal to or greater than the second frequency, then it is determined that the patient has moderate AS (Condition 4).

For example, 300 Hz and 180 Hz are set as the first frequency and the second frequency, respectively. At this time, the second processing portion 23 outputs a detection signal D5 indicating that there is a high probability of severe AS in a case where the peak frequency fp is 300 Hz or greater, and the second processing portion 23 outputs a detection auxiliary signal D6 indicating that there is a high probability of moderate AS in a case where the peak frequency fp is 180 Hz or greater and smaller than 300 Hz.

Based on the empirical study of previous cases, the peak frequency fp was in the range of 180 Hz to 300 Hz in cases of moderate AS. The peak waveform did not appear in cases of mild AS. Accordingly, in a case where the acquired peak frequency fp is in the range of 180 Hz to 300 Hz, there is a high probability of moderate AS.

Further, in the determination mode 4, it is possible to detect the severity of AS by determining whether it is highly likely to lead to severe AS in the future and whether echocardiography is to be made at the present time. This will be described next.

Figure 17:
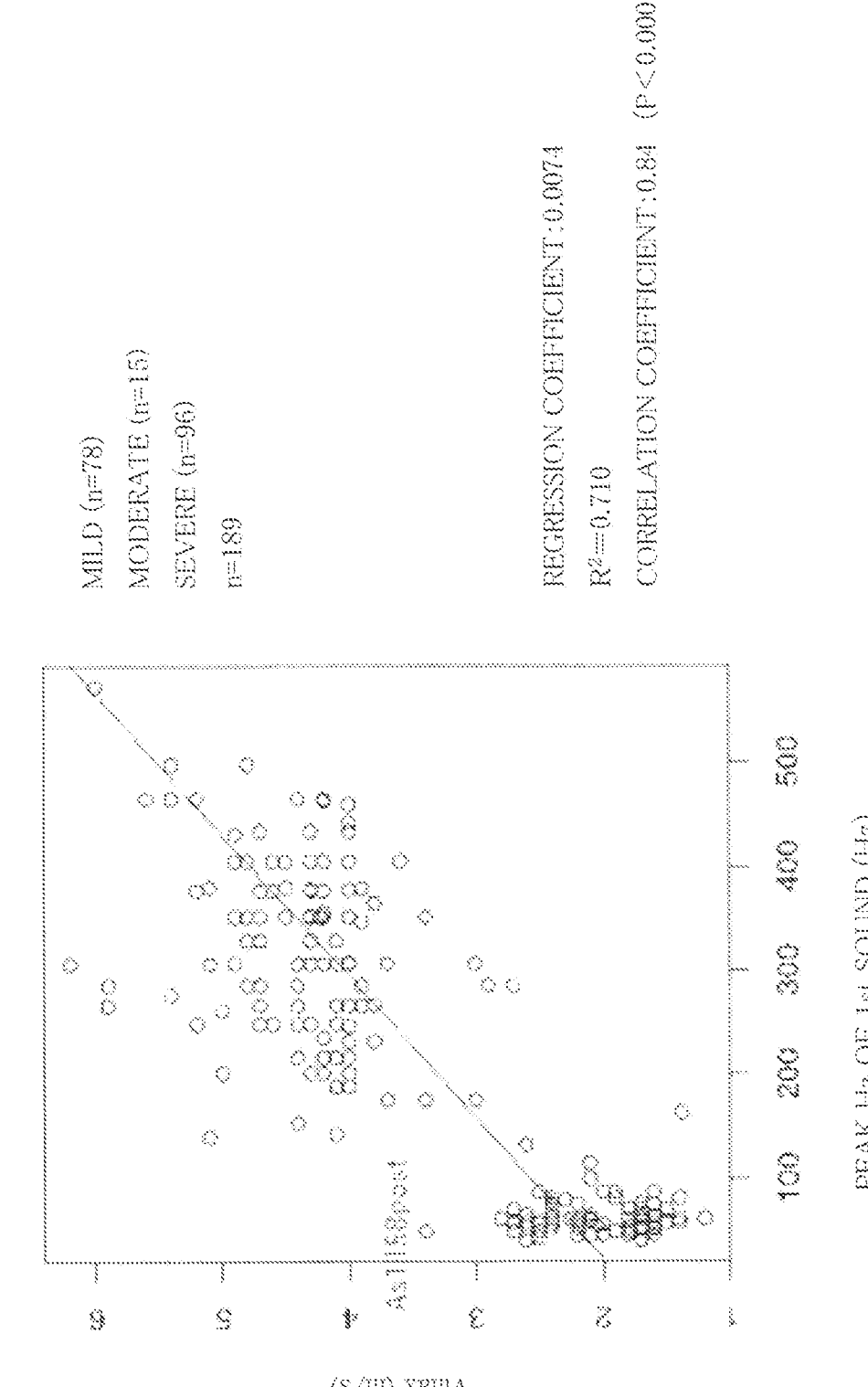
FIG. 17 is a diagram illustrating an example of a correlation between a peak frequency and aortic valve maximum blood flow velocity Vmax.

FIG. 17 is a plot diagram obtained by detecting peak frequencies fp for 189 cases (patients) with mild AS, moderate AS, and severe AS all included.

Referring to FIG. 17, the peak frequency fp (Hz) is represented by the horizontal axis and the aortic valve maximum blood flow velocity Vmax (m/sec) is represented by the vertical axis. Here, the aortic valve maximum blood flow velocity Vmax (hereinafter, referred to as "Vmax") was measured by continuous wave Doppler method for each case. Vmax is an important factor used in echocardiography to assess the severity of AS, and is detailed in "JCS/JATS/JSVS/JSCS 2020 Guideline on the Management of Valvular Heart Disease".

According to "Table 30: Assessment of the severity of AS by echocardiography" in Chapter 5, page 63 of "Guideline on the Management of Valvular Heart Disease", Vmax is 2.5 (m/sec) or smaller for "aortic valve sclerosis", Vmax is 2.6 to 2.9 for "mild AS", Vmax is 3.0 to 3.9 for "moderate AS", and Vmax is 4.0 or greater for "severe AS". In FIG. 17, 78 cases of "mild AS" (mild), 15 cases of "moderate AS" (moderate), and 96 cases of "severe AS" (severe) are shown according to the assessment criteria. Here, "mild AS" (mild) includes not only the original "mild AS", but also "aortic valve sclerosis" with milder symptoms and the normal group.

FIG. 17 indicates that the correlation coefficient is 0.84 and the peak frequency fp and Vmax have a strong positive correlation. To be specific, FIG. 17 indicates that Vmax tends to be high in cases where the peak frequency fp is high.

In most of the cases of "mild AS" (mild) having Vmax smaller than 3.0 (m/sec), the peak frequency fp is 150 Hz or smaller. In the case of using a regression line, the peak frequency fp corresponding to Vmax of 4.0 is approximately 300 Hz.

Based on the facts described above, it cannot be said that cases with a peak frequency fp of 150 Hz or greater are "mild AS", and therefore echocardiography should be performed in order to determine the severity. Further, it can be said that cases with a peak frequency fp of 150 Hz or greater and smaller than 300 Hz are highly likely to develop severe AS in the future. In the case of severe AS, surgery is highly likely to be performed; therefore, it can be said that the patients are a target group for which surgery should be considered in the future.

In light of the above, in a case where the peak frequency fp is 150 Hz or greater and smaller than 300 Hz, the second processing portion 23 outputs a detection auxiliary signal D6a indicating that the case is highly likely to develop severe aortic stenosis in the future. Further, in a case where the peak frequency fp is 150 Hz or greater, the second processing portion 23 outputs a detection auxiliary signal D6b indicating that echocardiography should be performed.

The detection auxiliary signal D6, the detection auxiliary signal D6a, and the detection auxiliary signal D6b include contents overlapping with each other. Using the individual signals with understanding of the meanings thereof allow for a quick and accurate response after the individual signals are indicated.

Further, for detection of the severities, as described next, not only the peak frequency fp but also the ejection time tk or the main frequency fm may be considered.

Further, the statistic use of the detection auxiliary signals D6, D6a, and D6b makes it possible to predict the approximate number of patients with severe AS or patients who should undergo surgery in the future, or to predict a tendency of increase/decrease in the number. This can be useful for manpower planning and facility planning in a hospital, or a national medical policy.

The determination in the determination mode 4 is preferably made by combining Conditions 2 and 3 used in the determination modes 2 and 3. In such a case, each parameter in Conditions 2 and 3 may be adjusted so that continuous detection is correctly performed according to the actual severity.

For example, in the case of combination with the conditions of the determination mode 2, if Condition 1 and Condition 2 are satisfied, then severe AS is determined. In the case of combination with the determination mode 2, if Condition 4 and Condition 2 are satisfied, then moderate AS is determined. At the determination of moderate AS, the value of the ejection reference value ce in Condition 2 can be adjusted to be lower than that in the case of severe AS.

This is because the ejection time tk in the case of moderate AS is considered to be smaller than that in the case of severe AS.

As described above, the heart valve abnormality detection device 5 can detect the severity of AS by combining Conditions 1 to 4 and adjusting the individual parameters.

Since the peak frequency fp, the ejection time tk, the main frequency fm, and the like are related not only to aortic stenosis but also to another valvular disease such as aortic valve insufficiency and mitral valve insufficiency and abnormalities in artificial valve, the present technology can be applied to detection of abnormalities and deterioration in various heart valves including an artificial valve.

Further, many sets of data such as the values of the peak frequency fp, the ejection time tk, and the main frequency fm, other test values, the actual symptoms, and the progress are given to artificial intelligence for learning, and the artificial intelligence can be used to diagnose the probability or severity of severe AS, detect abnormalities in various heart valves, or determine the degree of abnormality in various heart valves.

Figure 6:
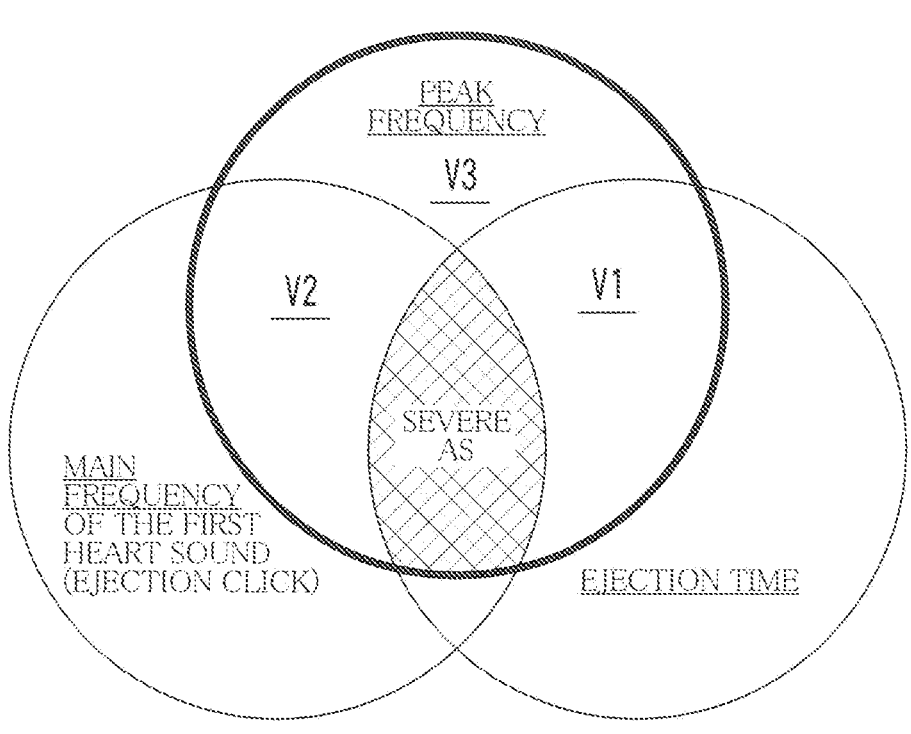
Figure 7:
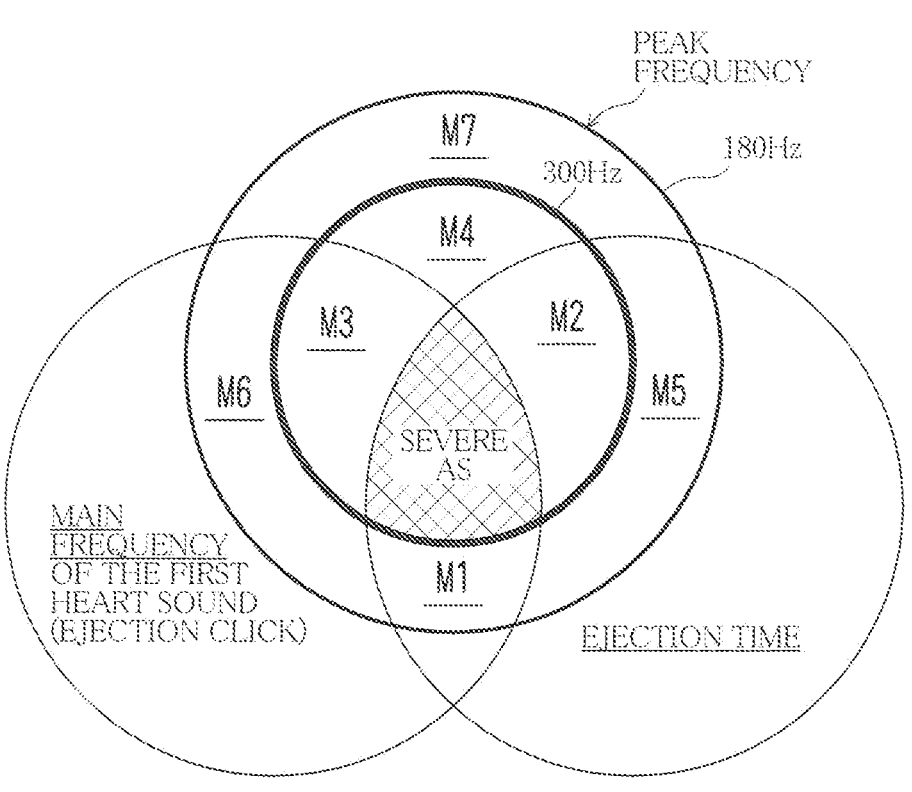
FIG. 7 is a conceptual diagram of an example of detection of the severity of AS in peak frequency diagnosis.

FIG. 6 is a conceptual diagram of an example of peak frequency diagnosis of severe AS. FIG. 7 is a conceptual diagram of an example of detection of the severity of AS in the peak frequency diagnosis.

Referring to FIG. 6, in a case where Condition 1 for the peak frequency fp, Condition 2 for the ejection time tk, and Condition 3 for the main frequency fm are satisfied at the same time, it is determined that the patient has severe AS. This corresponds to the determination mode 3. In such a case, as for a part V1 that satisfies Condition 1 and Condition 2 but does not satisfy Condition 3, a part V2 that satisfies Condition 1 and Condition 3 but does not satisfy Condition 2, and a part V3 that satisfies Condition 1 but does not satisfy Conditions 2 and 3, a signal indicating the corresponding state is preferably included in the detection signal D5. The parts V1, V2, and V3 can be treated as corresponding to, for example, severe AS, or suspected severe AS.

In FIG. 7, in a case where the peak frequency fp in Condition 3 is, for example, 300 Hz or greater, it is determined that the patient has severe AS. There are possible ways for determining moderate AS. For example, in a case where the peak frequency fp is in the range of 180 to 300 Hz, a part M1 that satisfies Condition 2 for the ejection time tk and Condition 3 for the main frequency fm are satisfied at the same time is determined to correspond to moderate AS. As for parts M2 to M7 that lacks any of the conditions, it is preferable to add a signal indicating that state to the detection auxiliary signal D6. The parts M2 to M7 can be treated as corresponding to, for example, moderate AS or suspected moderate AS.

Also, FIG. 7 illustrates a case where the peak frequency fp is 180 Hz or greater. By replacing "180 Hz" "150 Hz", it is applicable to detection of the severity of AS for a case where the peak frequency fp is 150 Hz or greater. In this case, for example, it is possible to determine that, as for the parts M1, M5 to M7, they correspond to cases that are highly likely to develop severe AS in the future and that surgery should be considered in the future. Alternatively, it is also possible to determine that the patient has suspected moderate AS.

The example in FIG. 7 corresponds to the determination mode 4 described above, and the severity of AS can be indicated according to the parts M2 to M7.

[Description of Scalogram by Wavelet Analysis]

Wavelet analysis was performed on the heart sound data D1 for some cases, and the results were illustrated in the form of scalogram (amplitude scalogram) in FIG. 8 to FIG. 15, which will be described next.

Figure 8:
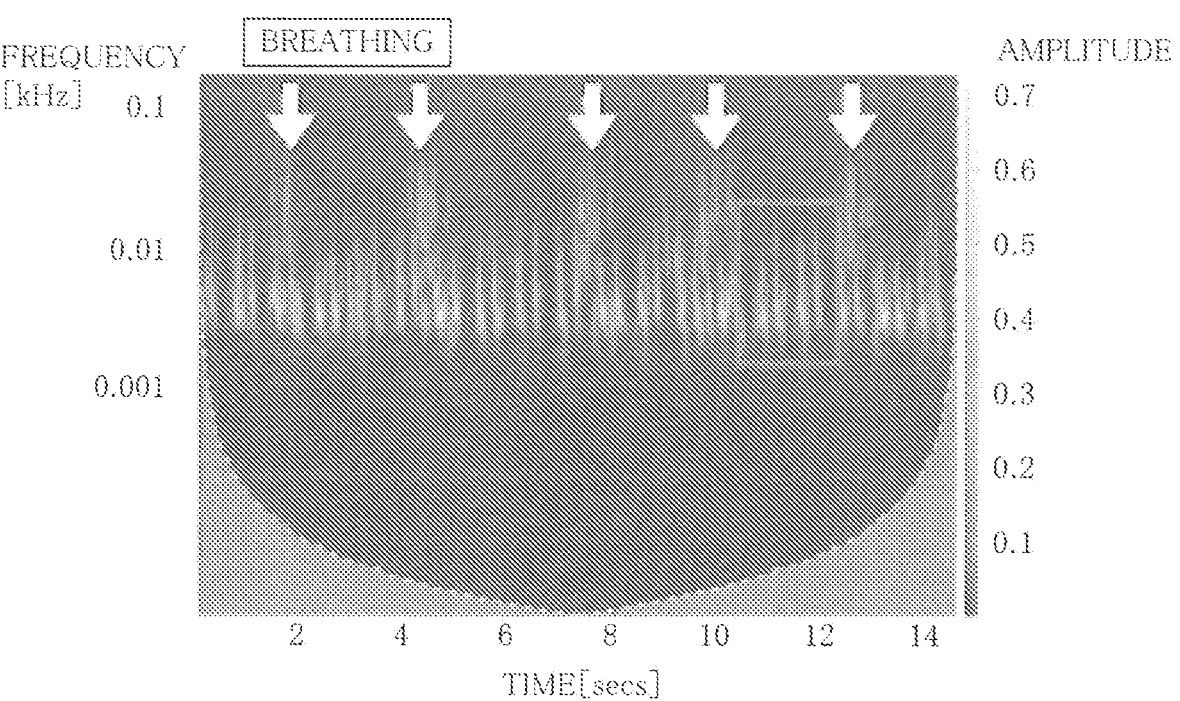
FIG. 8 illustrates an example of a result of wavelet analysis of normal heart sounds.
Figure 9:
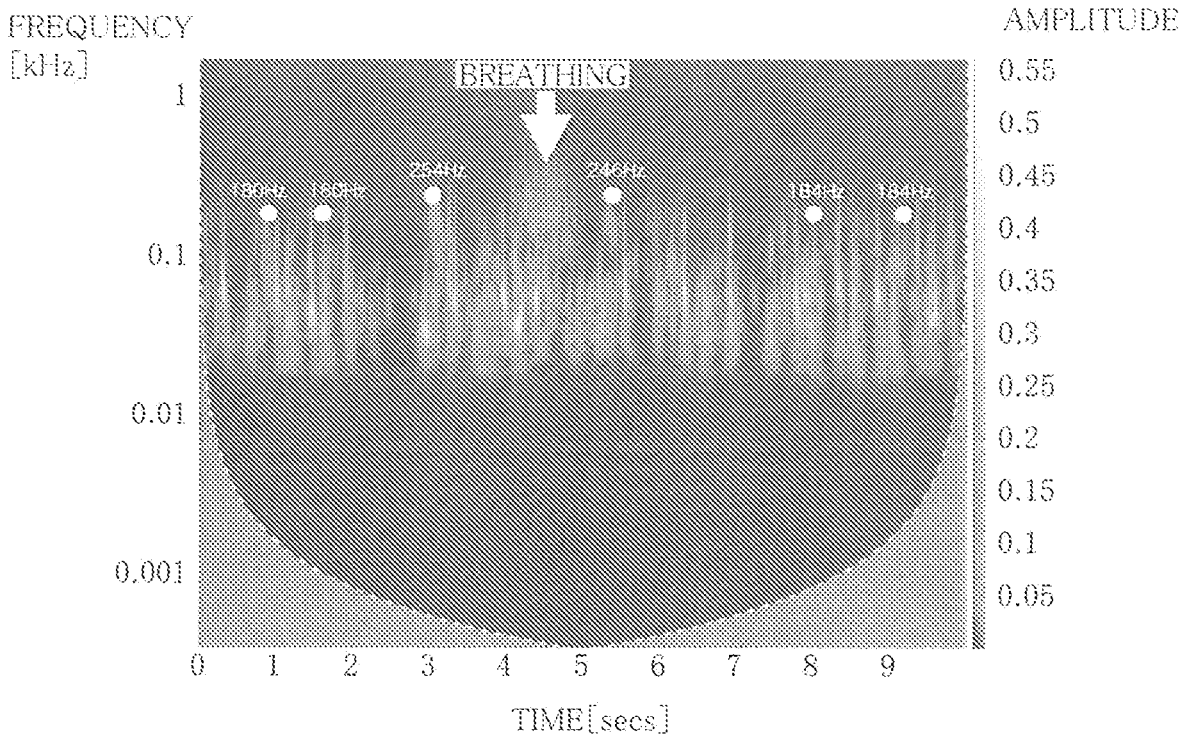
FIG. 9 illustrates an example of a result of wavelet analysis of moderate heart sounds.
Figure 10:
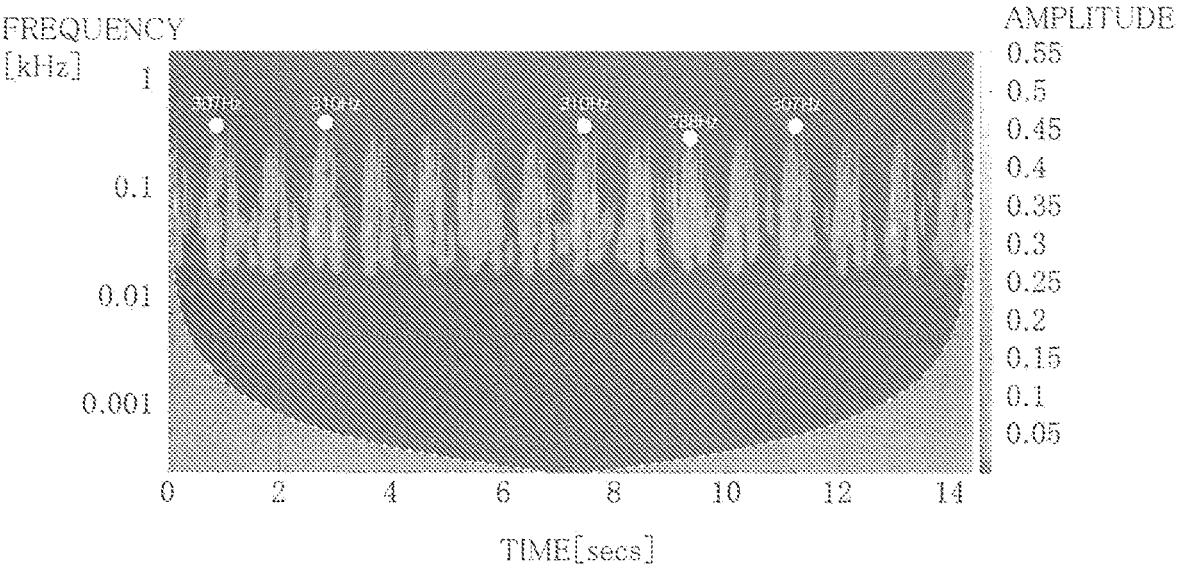
FIG. 10 illustrates an example of a result of wavelet analysis of severe heart sounds.
Figure 11:
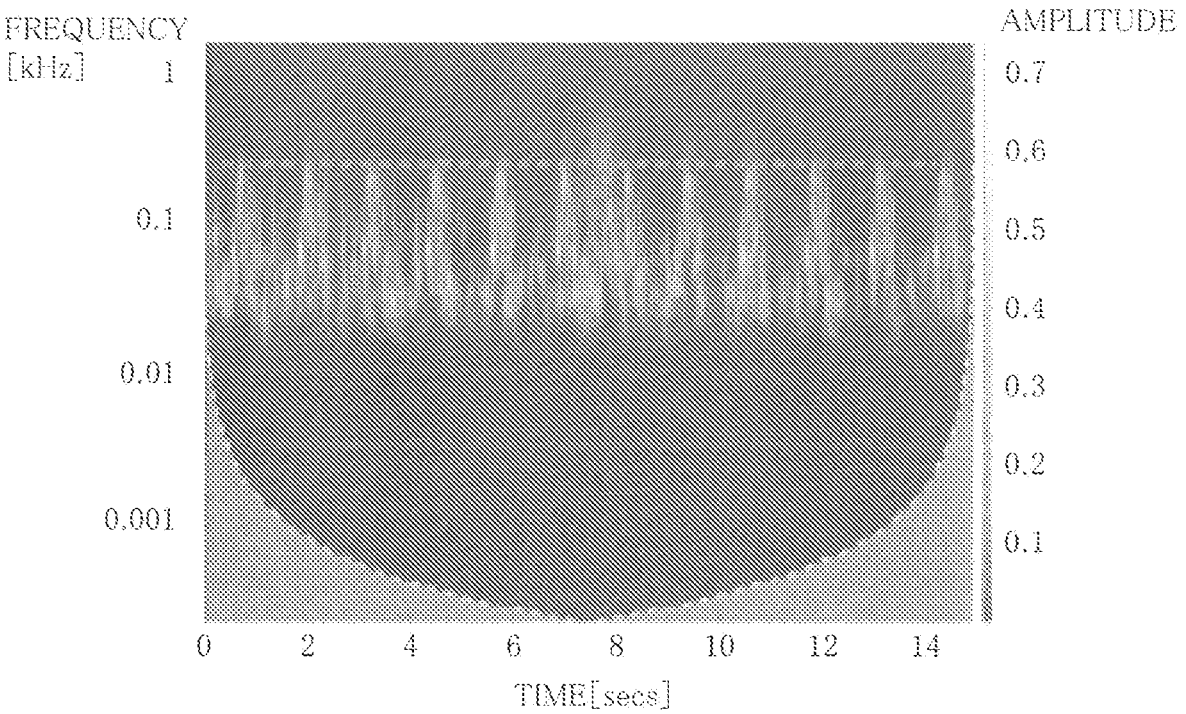
FIG. 11 illustrates another example of a result of wavelet analysis of severe heart sounds.
Figure 12:
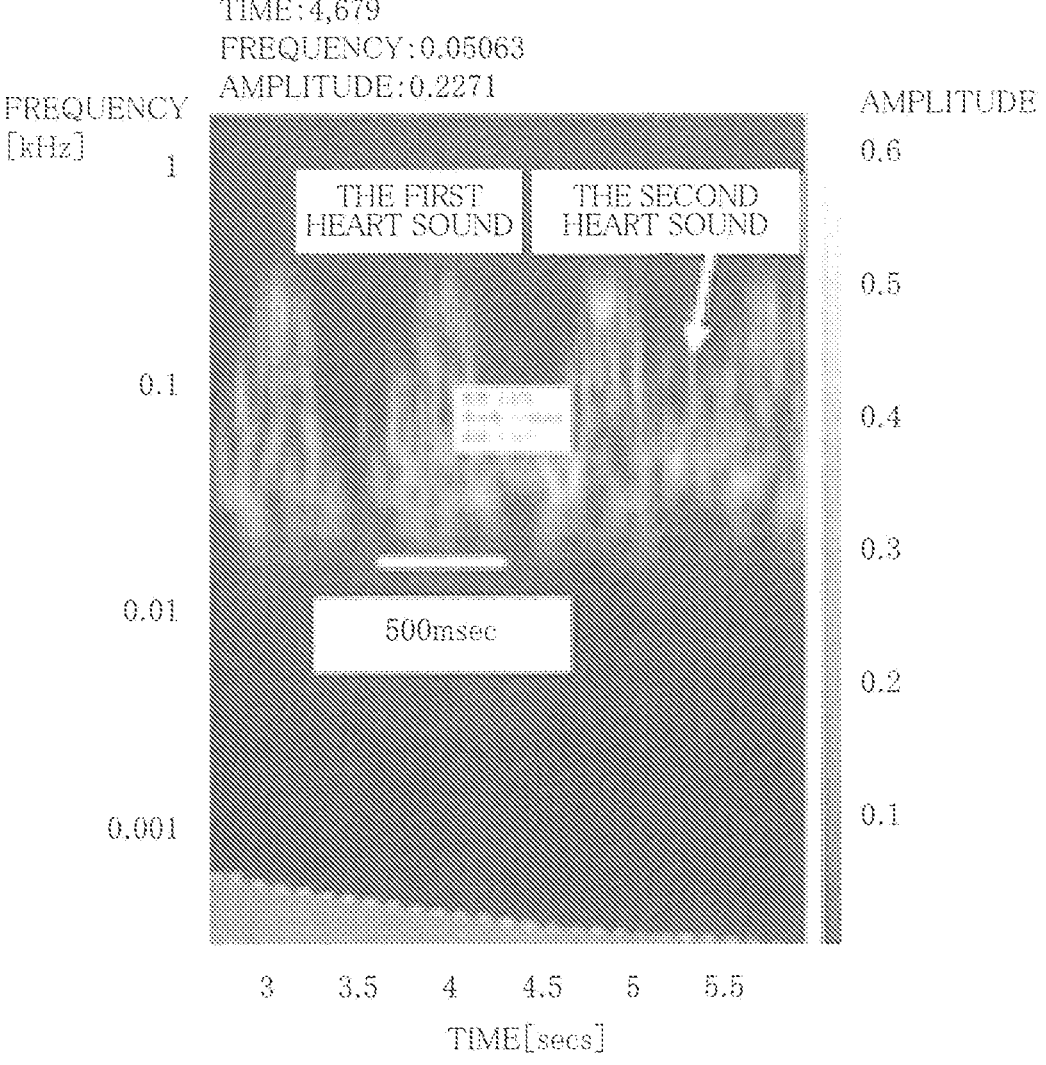
FIG. 12 is a partial enlarged view of a result of wavelet analysis of severe heart sounds.
Figure 13:
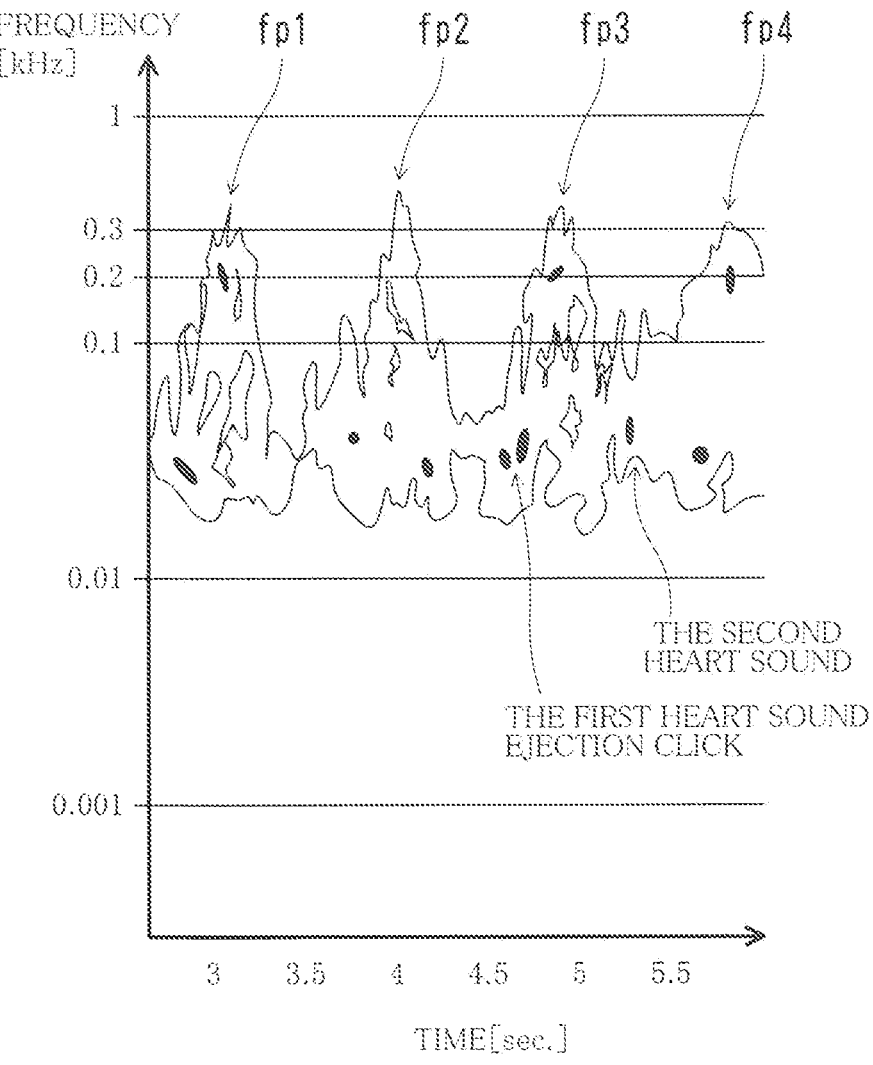
FIG. 13 is a diagram illustrating a result of wavelet analysis of severe heart sounds.
Figure 14:
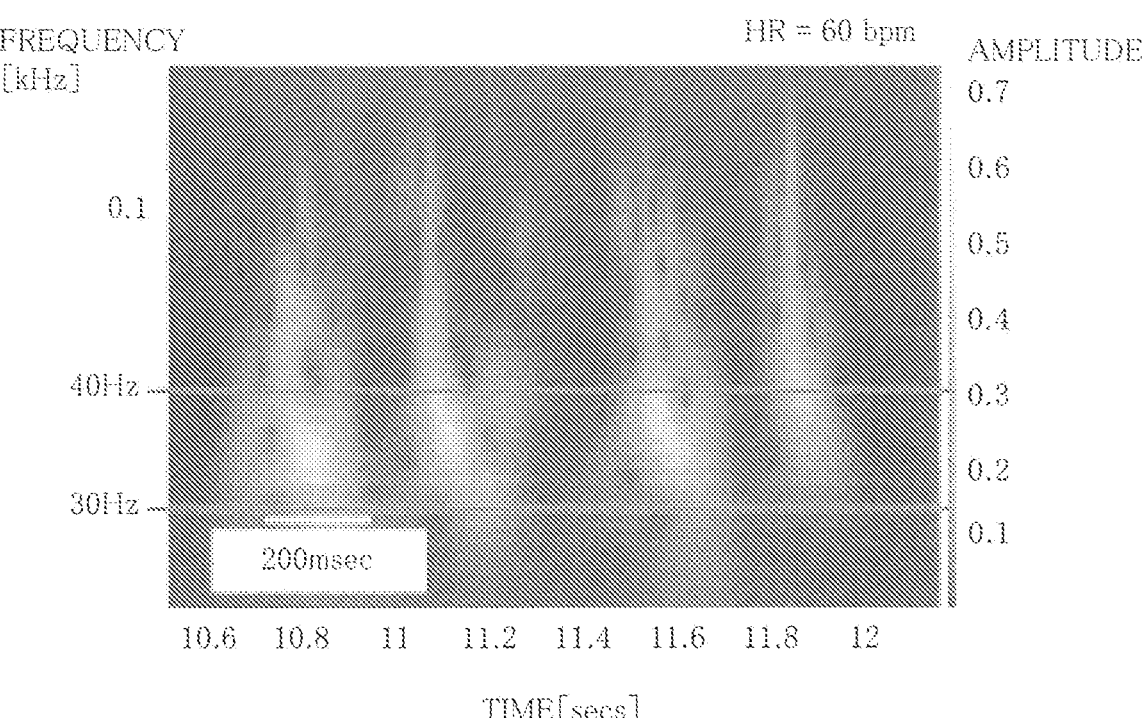
FIG. 14 is a partial enlarged view of a result of wavelet analysis of normal heart sounds.
Figure 15:
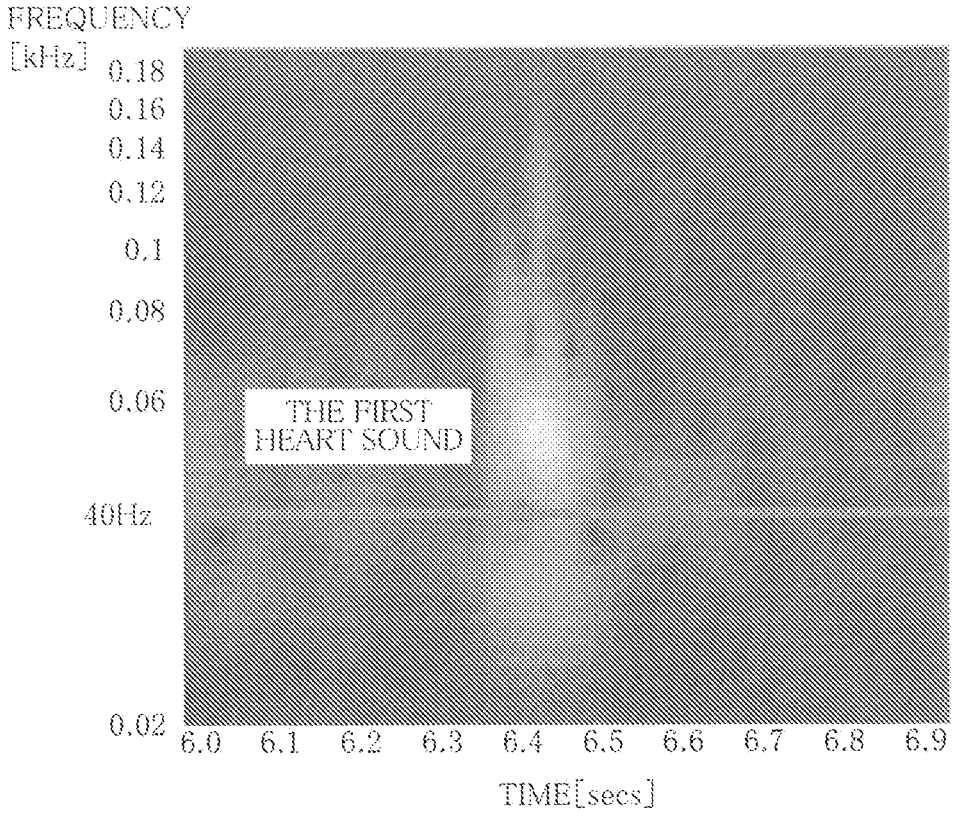
FIG. 15 is an enlarged view of a part of the first heart sound in a result of wavelet analysis of severe heart sounds.
Figure 16:
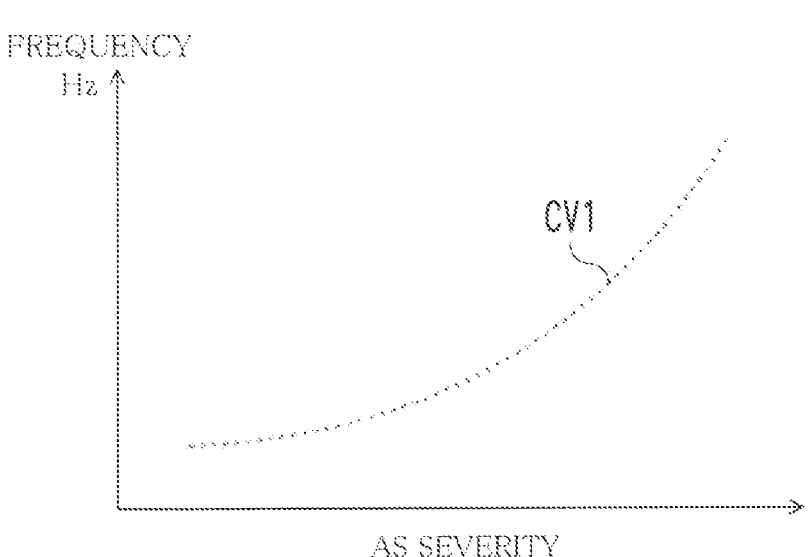
FIG. 16 is a diagram illustrating an example of a correlation between the severity in AS and peak frequency.

FIG. 8 illustrates an example of a result of wavelet analysis of normal heart sounds, FIG. 9 illustrates an example of a result of wavelet analysis of moderate heart sounds, FIG. 10 illustrates an example of a result of wavelet analysis of severe heart sounds, FIG. 11 illustrates another example of a result of wavelet analysis of severe heart sounds, FIG. 12 is a partial enlarged view of a result of wavelet analysis of severe heart sounds, FIG. 13 is a diagram illustrating a result of wavelet analysis of severe heart sounds, FIG. 14 is a partial enlarged view of a result of wavelet analysis of normal heart sounds, FIG. 15 is an enlarged view of a part of the first heart sound in a result of wavelet analysis of severe heart sounds, and FIG. 16 is a diagram illustrating an example of a correlation between the severity in AS and peak frequency.

In these figures, the horizontal axis represents a time (sec) on a linear scale and the vertical axis represents a frequency (kHz) on a logarithmic scale. The intensity (amplitude) is originally shown on a color scale that changes continuously from blue to green and then to yellow for better visibility; however, herein, the intensity is shown on a gray scale in which lightness changes continuously from black to white. For example, the intensity is normalized as 0 (zero) for black that has the lowest lightness and the intensity is normalized as 1 for white that has the highest lightness. Between black and white, the intensity is scaled according to the lightness, such as 0.1, 0.2, 0.3, . . . , and so on. Thus, it can be said that the lightness represents the intensity (amplitude) in the scalogram of the figures.

For example, in FIG. 8 illustrating a scalogram of normal heart sounds of a healthy individual, the first heart sound and the second heart sound in about 20 pulse waves during about 14 seconds along the horizontal axis are recorded. A part with an intensity (amplitude) of 0 (zero) is illustrated in black, and as the intensity increases, the lightness increases to approach white. The frequency of the first heart sound in the normal heart sounds of the healthy individual is approximately between 30 Hz and 40 Hz, and appears as a white dot with an intensity of approximately 0.6 to 0.7 between these frequencies on the vertical axis.

Referring to FIG. 8, it can be seen that a group of points with an intensity of approximately 0.2 to 0.5 rises, like flames, upward from the vicinity of the first heart sound and the second heart sound. The peak frequency fp of the normal heart sounds, namely, the frequency peak value in the frequency components of the normal heart sounds, is in the range of approximately 90 to 160 Hz, and the highest point of the group of points does not exceed 160 Hz.

Five arrows are indicated in the upper part of FIG. 8 and five spikes by a group of points with an intensity of approximately 0.3 are seen below the arrows. The peaks correspond to breath sounds, and have nothing to do with the heart sounds. It is thus necessary to exclude the breath sounds in order to acquire the peak frequency fp. Therefore, as described above, the noise removal portion 212 is used to remove the breath sounds as much as possible. However, in a case where the breath sounds cannot be completely removed and remains, the pulse wave that overlaps with the breath sounds is excluded when the peak frequency fp is acquired. The cycle of the breath sounds is almost constant, and the breath sounds are preferably determined based on the waveform.

In the scalogram for moderate heart sounds illustrated in FIG. 9, white dots for the first heart sound move slightly upward overall as compared with the case of normal heart sounds, and the peak frequency fp exceeds approximately 180 Hz.

In the scalograms for severe heart sounds illustrated in FIGS. 10 and 11, white dots for the first heart sound move further upward overall and a gap between the first heart sound and the second heart sound is wide as compared with the case of moderate heart sounds. There are spikes, following the first heart sound, of the frequency component of heart murmurs, and the highest point of each of the spikes is the peak frequency fp, and each of the peak frequencies fp exceeds approximately 300 Hz.

In FIGS. 9 to 11, the target range tr was set as an area between the first heart sound and the second heart sound. Peaks appearing, in addition to the peak frequency fp illustrated in the drawings, are either a peak outside the target range tr or a peak due to breath sounds, and such peaks are excluded from the target range tr. Further, in the example illustrated in FIG. 10, the top five peak frequencies were selected from the recorded heart rate and the representative value of the peak frequencies fp was determined by averaging the five peak frequencies. In this case, the representative value of the peak frequency fp is 304.4 Hz that is equal to or greater than the peak reference value cp of 300 Hz; therefore, it is determined that there is a high probability of severe AS.

FIGS. 12 and 13 illustrate spikes due to frequency components of four heart murmurs. The point having the highest intensity near the first heart sound (whitest point) indicates ejection click. The ejection click appears immediately after the first heart sound or together with the first heart sound, the frequency of the main component thereof is approximately 60 Hz, and it can be seen that, from there, a spike due to the frequency component of the heart murmur extends over a width of 280 ms to 500 ms. This spike is due to the occurrence of heart murmurs having a high frequency generated by the increased blood flow velocity resulting from the constriction of blood flow due to aortic stenosis, and the resulting peak frequency fp exceeds 300 Hz. At the same time, the ejection time is long such as approximately 280 ms to 500 ms, which causes a delay of generation of the second heart sound.

FIG. 14 illustrates the first heart sound and the second heart sound of normal heart sounds. It can be seen that the frequency of the first heart sound is between 30 Hz to 40 Hz. In FIG. 14, the heart rate is 60 bpm; however, in the scalogram of an example with a heart rate of 75 bpm, the frequency of the first heart sound was also between 30 Hz to 40 Hz.

FIG. 15 illustrates the first heart sound of severe heart sounds. It can be seen that the frequency of the first heart sound exceeds 40 Hz and reaches approximately 60 Hz.

As described above, according to the heart valve abnormality detection device 5 of the present embodiment, it is possible to easily detect an abnormality in a heart valve, in particular, severe aortic stenosis, with high accuracy and clear results. Further, it is possible to easily detect a degree of an abnormality in a heart valve with high accuracy and clear results.

Further, in particular, since the results can be acquired based only on the heart sound data D1 obtained by auscultation, easy implementation is possible without increasing the burden on a physician in a clinical practice or a patient. Severe AS can be determined by comparing the peak frequency fp acquired based on the heart sound data D1 with the peak reference value cp (peak frequency diagnosis); therefore, the determination result and the reason for determination are clear. Since the peak frequency fp can be easily acquired by wavelet analysis, the processing is simple, the processing time is short, and the processing can be performed at a relatively low cost. The detection accuracy can be further improved by feeding back the results of echocardiography and so on and adjusting the peak reference value cp, the ejection reference value ce, and the like.

In the meantime, as illustrated as a hypothetical curve CV1 in FIG. 16, it was found that the severity of AS has a positive correlation with the peak frequency fp. It is expected that, based on the founding, the severity of AS can be detected with a further higher degree of accuracy.

In the embodiments described above, the configuration of the heart valve abnormality detection device 5 can be changed in various ways. For example, the second processing portion 23 may output not only the detection results such as "moderate AS" and "severe AS" but also the severity according to the peak frequency fp, the ejection time tk, or the main frequency fm, namely, the progression of AS. Alternatively, the peak frequency fp, the ejection time tk, the main frequency fm, and so on may be output as they are.

In the embodiments described above, the heart valve abnormality detection device 5 can be implemented as a small home health appliance or as a portable device. A computer program to function as the heart valve abnormality detection device 5 may be executed by a personal computer or a smartphone, and the personal computer or the smartphone can be implemented as a heart valve abnormality detection device.

In order to implement the present invention as a method for detecting an abnormality in a heart valve, for example, beginning with the first processing portion 22, the second processing portion 23, the ejection time acquisition portion 24 and so on described above, the functions of each portion of the heart valve abnormality detection device 5 or the heart valve abnormality diagnosis system 1 are preferably implemented.

The configuration, the structure, the shape, the function, the setting value, the processing contents, the processing sequence, the output form of whole or each part of the heart sound data acquisition portion 21, the first processing portion 22, the second processing portion 23, the ejection time acquisition portion 24, the detection portion 25, the output/display portion 26, the heart valve abnormality detection device 5, the heart valve abnormality diagnosis system 1, and so on, or, the content, the signal format, the output timing of the detection signal D5, the detection auxiliary signal D6, and so on can be modified in various ways other than those described above.

REFERENCE SIGNS LIST

1 Heart valve abnormality detection system
5 Heart valve abnormality detection device
6 Heart sound sensor
7 Electrocardiograph
21 Heart sound data acquisition portion
22 First processing portion
23 Second processing portion
24 Ejection time acquisition portion
25 Detection portion
26 Output/display portion
211 Normalization portion
212 Noise removal portion
213 Amplification portion
D1 Heart sound data
D5 Detection signal D6 Detection auxiliary signal
fp Peak frequency
cp Peak reference value
tr Target range
ad reference intensity
fm Main frequency
cs First heart sound reference value
tk Ejection time
ce Ejection reference value
cf frequency range
The invention claimed is:

1. A heart valve abnormality detection device comprising:
a heart sound data acquisition unit configured to acquire heart sound data corresponding to heart sounds;
a first processing unit configured to acquire, based on the heart sound data, a peak frequency that is a peak value of a frequency in a frequency component of the heart sounds from a target range defined between a first heart sound and a second heart sound of the heart sounds;
an ejection time acquisition unit configured to acquire an ejection time based on the heart sound data;
a storage unit configured to store a first frequency that is a peak reference value for determining severe aortic stenosis (hereinafter as AS), a second frequency lower than the first frequency, and an ejection reference value; and
a second processing unit configured to output a detection signal D5 indicating severe AS when both the peak frequency is the first frequency or more and the ejection time is equal to or longer than the ejection reference value, and output a detection auxiliary signal D6 indicating moderate AS when both the peak frequency is lower than the first frequency and is equal to or higher than the second frequency and the ejection time is equal to or longer than the ejection reference value.

2. The heart valve abnormality detection device according to claim 1, wherein the first frequency is 300 Hz.

3. The heart valve abnormality detection device according to claim 2, wherein the second frequency is 180 Hz.

4. The heart valve abnormality detection device according to claim 2, wherein the second processing unit outputs a detection auxiliary signal D6$a$ indicating suspected severe AS when the peak frequency is 150 Hz or greater and is smaller than 300 Hz.

5. The heart valve abnormality detection device according to claim 1, wherein the second processing unit outputs a detection auxiliary signal D6$b$ indicating that echocardiography is to be performed when the peak frequency is 150 Hz or greater.

6. The heart valve abnormality detection device according to claim 1, wherein the target range is set to a range after 100 ms from a start of the first heart sound but not exceeding 500 ms.

7. The heart valve abnormality detection device according to claim 1, wherein, as the first frequency, a representative value that is determined based on a plurality of peak frequencies acquired from the target range for each of a plurality of pulse waves is used.

8. The heart valve abnormality detection device according to claim 1, wherein the ejection reference value is 280 ms.

9. The heart valve abnormality detection device according to claim 1, comprising a detection unit configured to detect, based on the heart sound data, ejection click occurring in a vicinity of the first heart sound, wherein
the second processing unit outputs the detection signal D5 when, in addition to a condition that the peak frequency is the first frequency or more and the ejection time is equal to or longer than the ejection reference value, a condition that the ejection click is detected is satisfied, and outputs the detection auxiliary signal D6 when, in addition to a condition that the peak frequency is lower than the first frequency and is equal to or higher than the second frequency and the ejection time is equal to or longer than the ejection reference value, a condition that the ejection click is detected is satisfied.

10. The heart valve abnormality detection device according to claim 9, wherein the detection unit detects a main frequency that is a frequency of a main component of the first heart sound, and detects the ejection click when the main frequency is a first heart sound reference value or greater.

11. The heart valve abnormality detection device according to claim 10, wherein the first heart sound reference value is 50 Hz.

12. The heart valve abnormality detection device according to claim 1, wherein, in acquiring the peak frequency, the first processing unit targets a frequency component of the heart sounds having an intensity equal to or greater than a reference intensity within the target range.

13. The heart valve abnormality detection device according to claim 1, wherein the first processing unit acquires the peak frequency by performing wavelet analysis on the heart sound data.

14. The heart valve abnormality detection device according to claim 1, wherein
the heart sound data acquisition unit includes
a normalization processing unit configured to normalize the heart sounds,
a noise removal unit configured to remove environmental noise, and
an amplification unit configured to perform amplification to a predetermined intensity level.

15. The heart valve abnormality detection device according to claim 1, wherein, in a state where the peak frequency is the second frequency or more and the ejection time is not equal to or longer than the ejection reference value, the detection auxiliary signal D6 is output with a signal indicating the state incorporated in the detection auxiliary signal D6.

16. The heart valve abnormality detection device according to claim 2, wherein, in a state where the peak frequency is the second frequency or more and the ejection time is not equal to or longer than the ejection reference value, the detection auxiliary signal D6 is output with a signal indicating the state incorporated in the detection auxiliary signal D6.

17. The heart valve abnormality detection device according to claim 3, wherein, in a state where the peak frequency is the second frequency or more and the ejection time is not equal to or longer than the ejection reference value, the detection auxiliary signal D6 is output with a signal indicating the state incorporated in the detection auxiliary signal D6.

18. The heart valve abnormality detection device according to claim 4, wherein, in a state where the peak frequency is the second frequency or more and the ejection time is not equal to or longer than the ejection reference value, the detection auxiliary signal D6 is output with a signal indicating the state incorporated in the detection auxiliary signal D6.

19. The heart valve abnormality detection device according to claim 9, wherein, in a state where the peak frequency is the second frequency or more and either the ejection time is not equal to or longer than the ejection reference value or the ejection click is not detected, the detection auxiliary signal D6 is output with a signal indicating the state incorporated in the detection auxiliary signal D6.

20. A non-transitory recording medium storing a computer readable program used in a computer, the computer readable program causing the computer to perform processing comprising:

first processing for acquiring heart sound data corresponding to heart sounds;

second processing for acquiring, based on the heart sound data, a peak frequency that is a peak value of a frequency in a frequency component of the heart sounds from a target range defined between a first heart sound and a second heart sound of the heart sounds;

third processing for acquiring an ejection time based on the heart sound data;

fourth processing for storing a first frequency that is a peak reference value for determining severe aortic stenosis (hereinafter as AS), a second frequency lower than the first frequency, and an ejection reference value; and fifth processing for outputting a detection signal D5 indicating severe AS when both the peak frequency is the first frequency or more and the ejection time is equal to or longer than the ejection reference value, and outputting a detection auxiliary signal D6 indicating moderate AS when both the peak frequency is lower than the first frequency and is equal to or higher than the second frequency and the ejection time is equal to or longer than the ejection reference value.

21. A method for detecting an abnormality in a heart valve by processing heart sound data corresponding to heart sounds, the method comprising:

performing first processing of acquiring, based on the heart sound data, a peak frequency that is a peak value of a frequency in a frequency component of the heart sounds from a target range defined between a first heart sound and a second heart sound of the heart sounds;

performing ejection time acquisition processing of acquiring an ejection time based on the heart sound data; and performing second processing of using a first frequency that is a peak reference value for determining severe aortic stenosis (hereinafter as AS), a second frequency lower than the first frequency, and an ejection reference value that are stored in a storage unit to output a detection signal D5 indicating severe AS when both the peak frequency is the first frequency or more and the ejection time is equal to or longer than the ejection reference value, and output a detection auxiliary signal D6 indicating moderate AS when both the peak frequency is lower than the first frequency and is equal to or higher than the second frequency and the ejection time is equal to or longer than the ejection reference value.

\* \* \* \* \*